US011109831B2

(12) United States Patent
Eibl et al.

(10) Patent No.: US 11,109,831 B2
(45) Date of Patent: Sep. 7, 2021

(54) ULTRASOUND PATCH FOR DETECTING FLUID FLOW

(71) Applicant: 1929803 Ontario Corporation, Sudbury (CA)

(72) Inventors: Joseph Eibl, Sudbury (CA); Jon-Emile S. Kenny, Sudbury (CA); Christine Demore, Toronto (CA); Chelsea Munding, Sudbury (CA); Jeremy Brown, Halifax (CA); Aaron Boyes, Toronto (CA)

(73) Assignee: 1929803 Ontario Corp, (o/a FloSonics Medical), Sudbury (CA)

( * ) Notice: Subject to any disclaimer, the term of this patent is extended or adjusted under 35 U.S.C. 154(b) by 0 days.

(21) Appl. No.: 16/377,028

(22) Filed: Apr. 5, 2019

(65) Prior Publication Data

US 2020/0022670 A1 Jan. 23, 2020

Related U.S. Application Data

(60) Provisional application No. 62/699,571, filed on Jul. 17, 2018.

(51) Int. Cl.
*A61B 8/06* (2006.01)
*A61B 8/00* (2006.01)
*A61B 8/08* (2006.01)

(52) U.S. Cl.
CPC .............. *A61B 8/06* (2013.01); *A61B 8/4281* (2013.01); *A61B 8/488* (2013.01); *A61B 8/56* (2013.01)

(58) Field of Classification Search
None
See application file for complete search history.

(56) References Cited

U.S. PATENT DOCUMENTS 4,103,679 A 8/1978 Aronson
4,189,655 A * 2/1980 Bruel .................... B06B 1/0651 310/329

(Continued)

FOREIGN PATENT DOCUMENTS

CA 2950919 A1 1/2016
WO WO2008042559 A2 4/2008

(Continued)

OTHER PUBLICATIONS

International Search Report and Written Opinion for International Application No. PCT/CA2019/050918; dated Sep. 23, 2019; 11 pages.

(Continued)

*Primary Examiner* — Yi-Shan Yang
(74) *Attorney, Agent, or Firm* — Perkins Coie LLP

(57) ABSTRACT

An ultrasound patch includes one or more transmit and receive piezoelectric transducer elements. In some embodiments, the transducer elements are positioned on a ramp on a patient pad of the patch that is configured to fit within an anatomic space between the trachea and the sternocleidomastoid muscle to orient the transducer elements toward a carotid artery. In some embodiments, a flexible phased array transducer includes a number of pillar piezoelectric elements joined by a flexible adhesive with metal electrodes deposited thereon. The phased array transducer is mounted to a flexible circuit board that allows the transducer to bend and conform to a subject's anatomy.

20 Claims, 41 Drawing Sheets

(56) References Cited

U.S. PATENT DOCUMENTS

| | | | | |
|---|---|---|---|---|
| 5,113,867 | A | 5/1992 | Janszen | |
| 10,394,209 | B2 | 8/2019 | Goodon et al. | |
| 2001/0021817 | A1 | 9/2001 | Brugger et al. | |
| 2002/0042574 | A1 | 4/2002 | Manor et al. | |
| 2005/0156491 | A1* | 7/2005 | Scott | B06B 1/064 310/334 |
| 2006/0206032 | A1 | 9/2006 | Miele et al. | |
| 2006/0264756 | A1* | 11/2006 | Lo | A61B 8/14 600/459 |
| 2008/0208273 | A1 | 8/2008 | Owen et al. | |
| 2010/0016725 | A1* | 1/2010 | Thiele | G01S 7/52077 600/447 |
| 2010/0022886 | A1* | 1/2010 | Ayati | G09B 23/288 600/454 |
| 2010/0049052 | A1 | 2/2010 | Sharf et al. | |
| 2010/0076315 | A1 | 3/2010 | Erkamp et al. | |
| 2010/0160784 | A1 | 6/2010 | Poland et al. | |
| 2011/0137173 | A1* | 6/2011 | Lowe | A61B 5/02152 600/454 |
| 2012/0138533 | A1 | 6/2012 | Curtis et al. | |
| 2012/0184854 | A1 | 7/2012 | Raju et al. | |
| 2012/0277640 | A1 | 11/2012 | Lewis, Jr. et al. | |
| 2012/0296216 | A1 | 11/2012 | Sharf et al. | |
| 2013/0116571 | A1 | 5/2013 | Cox | |
| 2013/0144166 | A1 | 6/2013 | Specht et al. | |
| 2014/0058259 | A1 | 2/2014 | Liu | |
| 2014/0081144 | A1 | 3/2014 | Moehring et al. | |
| 2014/0371594 | A1 | 12/2014 | Flynn et al. | |
| 2015/0009782 | A1 | 1/2015 | Engl et al. | |
| 2015/0135840 | A1* | 5/2015 | Sato | A61N 7/00 73/644 |
| 2015/0272513 | A1 | 10/2015 | Tan et al. | |
| 2015/0289838 | A1 | 10/2015 | Nichol et al. | |
| 2016/0206292 | A1* | 7/2016 | Vezina | A61B 8/00 |
| 2016/0351783 | A1* | 12/2016 | Chang | H01L 41/337 |
| 2017/0049413 | A1 | 2/2017 | Nichol et al. | |
| 2017/0080255 | A1 | 3/2017 | Law et al. | |
| 2017/0110504 | A1* | 4/2017 | Panchawagh | H01L 27/20 |
| 2017/0293277 | A1 | 10/2017 | Goodon et al. | |
| 2017/0325328 | A1* | 11/2017 | Isaac | H05K 1/0296 |
| 2018/0020982 | A1* | 1/2018 | Elsherbini | A61B 5/0205 600/301 |
| 2018/0206819 | A1* | 7/2018 | Saarinen | A61B 8/4444 |
| 2018/0353157 | A1 | 12/2018 | Eibl et al. | |
| 2019/0021659 | A1* | 1/2019 | Sajwan | A61B 5/0402 |
| 2019/0059848 | A1* | 2/2019 | Owen | A61B 8/0833 |

FOREIGN PATENT DOCUMENTS

| | | | | |
|---|---|---|---|---|
| WO | WO-2009154298 | A1 * | 12/2009 | A61B 5/0095 |
| WO | WO2015074015 | A1 | 5/2015 | |
| WO | WO2015181167 | A1 | 12/2015 | |
| WO | WO-2017096487 | A1 * | 6/2017 | A61B 5/026 |

OTHER PUBLICATIONS

Blanco et al., “Rapid Ultrasound in Shock (RUSH) Velocity-Time Integral”, J Ultrasound Med., vol. 34, pp. 1691-1700, Aug. 2015.

* cited by examiner

Doppler Shift at rest for carotid artery

ULTRASOUND PATCH FOR DETECTING FLUID FLOW

RELATED APPLICATIONS

The present application claims the benefit of, and priority to, U.S. Provisional Patent Application No. 62/699,571 filed Jul. 17, 2018, which is herein incorporated by reference in its entirety.

TECHNICAL FIELD

The disclosed technology relates to ultrasound devices designed to detect fluid flow in a vessel.

BACKGROUND

In many clinical and diagnostic settings, physicians or other medical personnel often use ultrasound to assess how well blood is flowing through a subject's vasculature. Most ultrasound systems require that an operator use one hand to hold an ultrasound transducer at a particular angle to a vessel while using the other hand to control a base unit of the ultrasound imaging system, thereby preventing the performance of other tasks while measuring flow. Another approach to measuring flow is to use a dedicated ultrasound flow measuring device such as described in PCT/CA2016/051451, US 2017-0293277 A1 and U.S. patent application Ser. No. 15/877,251, filed Jan. 22, 2018, (published as U.S. 2018-0353157 A1), which are herein incorporated by reference in their entireties. The devices described in these applications can be affixed to a subject to continuously or periodically measure flow in a vessel thereby freeing up the hands of the caregiver.

The disclosed technology relates to improvements in the design of the transducers for use in such a dedicated ultrasound flow measuring device (also referred to as an ultrasound patch) and for use of such a flow measuring device to measure flow in a vessel, changes in velocity to estimate changes in vessel diameter and central venous pressure (CVP), and changes to detect a relationship between Doppler flow and hemodynamic pathologies including sepsis, shock and congestive heart failure (CHF).

SUMMARY

As will be described in detail below, the disclosed technology relates to ultrasound transducers that are configured to measure flow in a vessel. In some embodiments, a transducer includes one or more transmit (TX) transducer elements that are spaced from one or more receive (RX) transducer elements. The transducer elements direct ultrasound energy into a subject and receive echo signals from moving body fluids (e.g. blood). In some embodiments, the transmit and receive transducer elements are arranged in a frame having an open back so that the rear surface of the transducer elements are not enclosed or have an air gap behind the transducers. A printed circuit board includes electrical traces for signal connections to the transducer elements and traces for a common ground connection or can be wired into a selective mixer to select a channel with the best signal to noise ratio for either a forward or reverse channel.

For some applications, the transducers are mounted on a ramp to mechanically tilt the transducers for carotid velocimetry and flow monitoring. In some embodiments, the transducers are mounted to an elastomeric patient pad that includes a ramp that sets the transducers at an angle with respect to flow in a vessel to be measured. In other embodiments, such as for use with compression garments for patients with circulatory disfunction, a flat surfaced transducer with lensing or a phased array transducer is more appropriate so as not to create a pressure point.

BRIEF DESCRIPTION OF THE DRAWINGS

FIGS. 6A-6K show a structure of an air-backed transducer and a method for manufacturing a number of air-backed transducers in accordance with some embodiments of the disclosed technology;

DETAILED DESCRIPTION

The disclosed technology relates to improved transducer designs for use with an ultrasound patch device that is configured to detect flow in a vessel. As will be discussed in detail below, in some embodiments, the transducers include air or foam-backed piezoelectric elements that produce ultrasonic acoustic energy for delivery towards a vessel and produce electronic signals from the corresponding acoustic echo signals received.

Figure 1B:
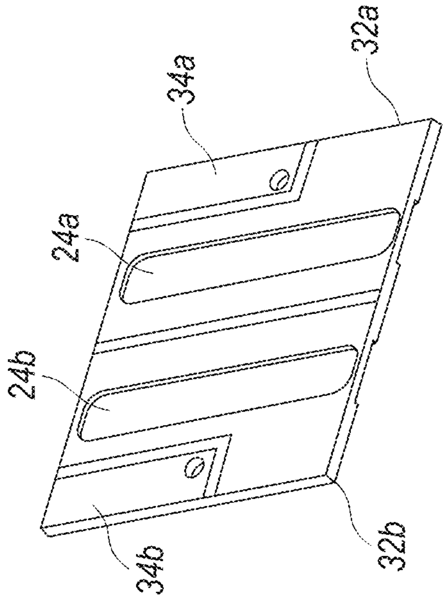
FIGS. 1A and 1B are front and rear isometric views of a printed circuit board that supports an air-backed array of ultrasound transducer elements in accordance with one embodiment of the disclosed technology.
Figure 1A:
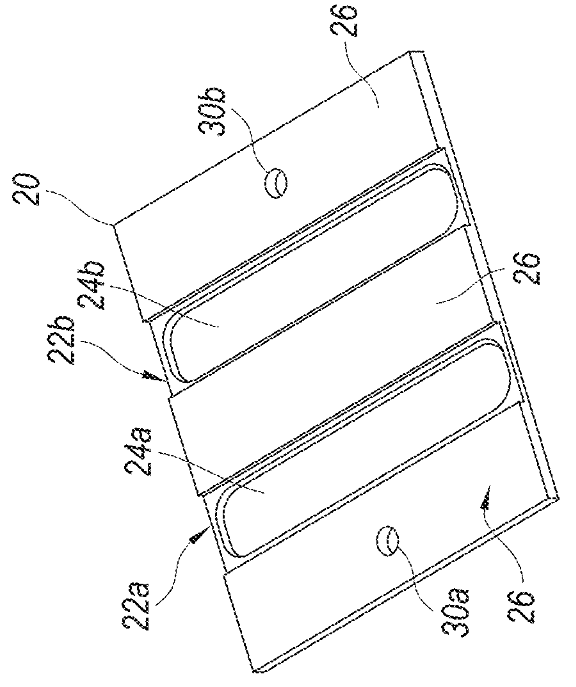

FIGS. 1A and 1B are isometric front and back views of a printed circuit board 20 that is configured to support a pair of piezoelectric transducer elements. In one embodiment, the circuit board 20 is rectangular and includes a pair of spaced, parallel milled slots 22*a*, 22*b*, running from one edge to another edge. Each slot includes an opening or hole 24*a*, 24*b* that is nearly the size of the slot and extends through the printed circuit board. The holes 24*a*, 24*b* provide an opening to the rear surface of the transducer elements (not shown) when they are mounted in the slots on the printed circuit board. In one embodiment, the circuit board 20 is about 3 cm. on each side although the printed circuit board could be made larger or smaller.

In the embodiment shown, a top surface of the printed circuit board 20 includes a common ground electrode 26 made of a conductive material such as gold, copper or aluminum. In the embodiment show, the common ground electrode covers the entire top surface of the printed circuit board except for the area of the milled slots 22. A pair of through holes or vias 30*a*, 30*b* extend from the top surface of the board to the rear surface of the board for an electrical connection to the ground electrode on the front of the printed circuit board.

FIG. 1B shows a rear surface of the printed circuit board 20 shown in FIG. 1A. The rear surface includes a pair of signal electrodes 32*a*, 32*b* surrounding each of the back sides of the slots and the openings 24*a*, 24*b*. In this embodiment, the signal electrodes 32*a*, 32*b* are not electrically connected to each other so that the transducer elements on the front surface of the printed circuit board can be driven separately. The rear surface of the printed circuit board also includes a pair of ground electrodes 34*a*, 34*b*. In one embodiment, these ground electrodes 34*a*, 34*b* on the back side of the printed circuit board are electrically coupled to the ground electrodes 26 on the front surface of the printed circuit board through the vias 30*a*, 30*b* or another conductive path.

Figure 2B:
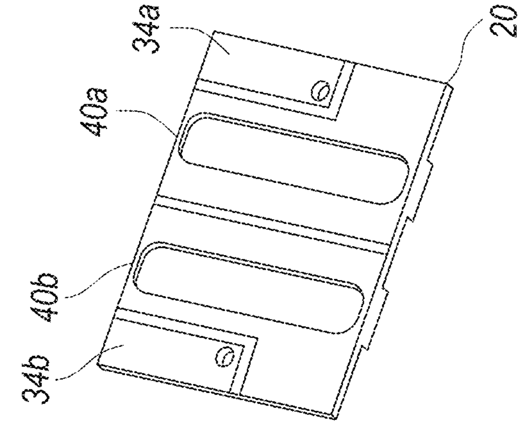
FIGS. 2A and 2B are front and rear isometric views of a pair of piezoelectric transducer elements secured to the printed circuit board shown in FIGS. 1A and 1B.
Figure 2A:
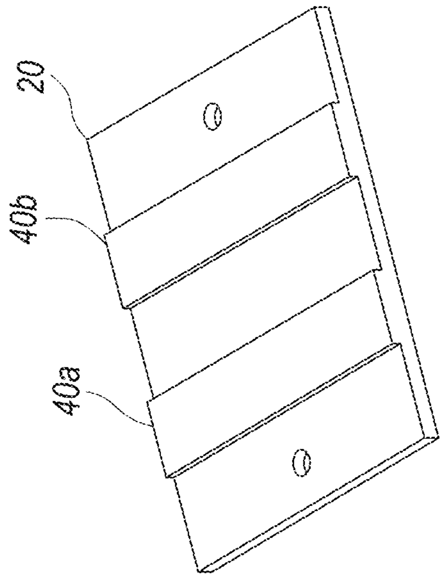

FIGS. 2A and 2B show the printed circuit board of FIGS. 1A, 1B with a pair of transducer elements 40*a*, 40*b* secured thereto. In the embodiment shown, each of the transducers elements 40*a*, 40*b* comprises a rectangular sheet of lead zirconate titanate (PZT) or other piezoelectric material. The transducer elements 40*a*, 40*b* are secured in the slots of the printed circuit board with a non-conductive epoxy. The top and bottom surfaces of the transducer elements include a conductive electrode such as a metallic coating (gold, copper or the like). FIG. 2B shows the printed circuit board 20 with the transducer elements 40*a*, 40*b* secured in the slots and the openings 24*a*, 24*b* aligned with rear surface of the transducer elements. In one embodiment, the electrodes on the PZT sheets are electrically connected to the conductive traces on the printed circuit board 20 with a conductive epoxy such as EPO-TEK H20E that bridges the gap between the surface of the printed circuit board and the electrodes on the PZT sheets. In other embodiments, a metal foil or other conductor could be used to electrically connect the traces on the printed circuit board to the electrodes on the transducer elements. In one embodiment, micro-coaxial conductors (not shown) are connected to the signal electrodes. In one embodiment, the signal electrodes for each transducer element are electrically separate while the ground electrodes on the printed circuit board and the transducer elements are commonly connected.

In the embodiment shown, the ground electrodes on the transducer elements are facing forward and the signal electrodes are on the rear surface. It will be appreciated that this could be reversed with the ground electrode on the rear surface and the signal electrodes on the front surface.

Figure 3B:
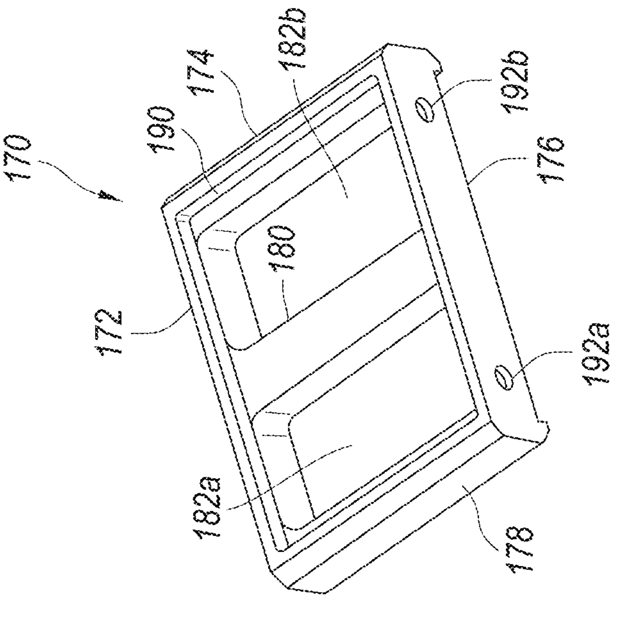
FIGS. 3A and 3B are isometric views of two different embodiments of a frame that supports the air-backed transducer elements in accordance with embodiments of the disclosed technology.
Figure 3A:
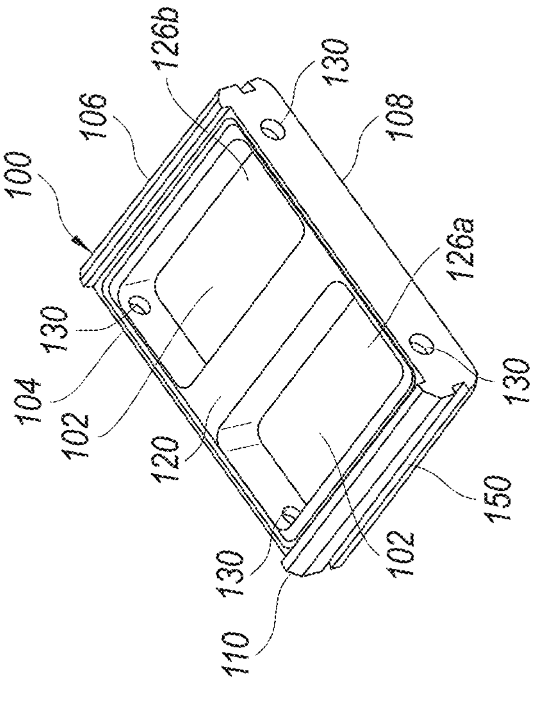

FIGS. 3A and 3B show two embodiments of a frame that supports the printed circuit board and the transducer elements. As shown in FIG. 3A, a frame 100 includes bottom floor 102 and a set of sidewalls 104, 106, 108, 110 that extend outwardly from the bottom floor and surround the perimeter of the bottom floor 102. A center beam 120 connects the sidewall 104 to the sidewall 108 and divides the open space between the sidewalls of the frame into a first cavity 126*a* and a second cavity 126*b*. In one embodiment, the cavities 126*a*, 126*b* are air filled and are aligned behind the exposed rear surfaces of the transducer elements. The sidewalls 104 and 108 also include pairs of aligned holes 130 through which a micro-coaxial cable or other conductor can be passed. The top perimeter of the sidewalls 104, 106, 108, 110 includes a lip around the interior of the edge that is sized to receive the perimeter of the printed circuit board 20 shown in FIGS. 1A, 1B, 2A, 2B. In some embodiments, the printed circuit board 20 is held in the frame 100 with an adhesive.

In the embodiment shown in FIG. 3A, the sidewalls 106, 110 include a horizontally extending groove 150 on the exterior of opposing sidewalls 106, 110 that is configured to receive a flexible member such a metal, plastic or graphite rod in order to keep multiple frames aligned as will be explained in further detail below.

In the embodiment shown in FIG. 3B, a frame 170 is formed without the bottom floor. In this embodiment, the frame 170 includes four connected sidewalls 172, 174, 176, 178 where the sidewalls 172 and 176 are joined by a center beam 180 that divides the open space between the sidewalls into a pair of cavities 182*a*, 182*b*. A lip 190 around the interior of the top surface of the sidewalls is sized to receive the outer perimeter of the printed circuit board so that the printed circuit board can be secured to the frame 170 with an adhesive or the like. The sidewall 176 also includes pair of holes 192*a*, 192*b* through which electrical connectors such as micro-coaxial cables can pass. In the embodiment shown, the holes 192*a*, 192*b* are only on the sidewall 176 and therefore the frame is not designed to be electrically connected to other frames. In this embodiment, because the frame 170 lacks a bottom floor, the cavities 182*a*, 182*b* are open to the air.

Figure 4A:
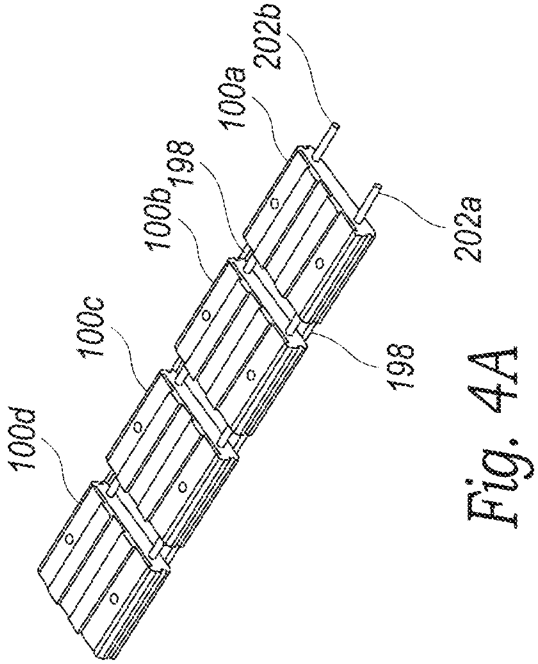
FIG. 4A shows a number of transducer frames connected with co-axial cables in accordance with an embodiment of the disclosed technology.

FIG. 4A shows a number of frames 100*a*, 100*b*, 100*c*, 100*d* that are positioned side by side in a line. A pair of flexible alignment members 198 such as flexible metal, plastic or graphite rods are positioned in the sidewall grooves of each frame to align the frames and to permit the frames to bend and conform to a curved shape of a subject's anatomy. A set of conductors such as micro-coaxial cables 202*a*, 202*b* electrically connect the transducer elements in each frame in parallel. In one embodiment, one transducer element in each frame is a transmit (TX) element and the other transducer element is a receive (RX) element. In one embodiment, all the TX transducer elements of the aligned frames are connected in parallel while all the RX transducer elements are connected in parallel. In other embodiments, each of the TX and RX elements can be controlled separately. This has the benefit of being to select a TX/RX pair that is best positioned over a desired vessel to produce the signals required to analyze flow.

Figure 4B:
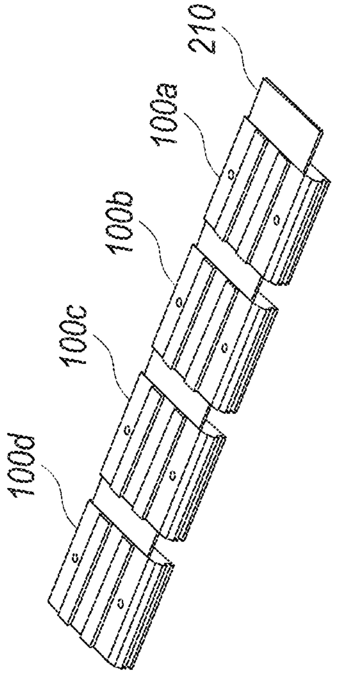
FIG. 4B shows a number of transducer frames connected by a flex circuit in accordance with an embodiment of the disclosed technology.

FIG. 4B shows an alternative embodiment where a series of four frames 100*a*, 100*b*, 100*c*, 100*d* are connected by a flex circuit 210 including traces that electrically connect the transducer elements together. In one embodiment, the TX elements of each frame are electrically connected in parallel and the RX elements are electrically connected in parallel. However, traces in the flex circuit could connect to each transducer element individually.

Figure 4C:
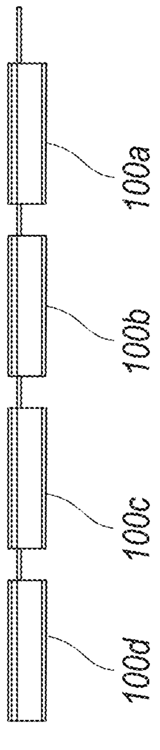
FIG. 4C is a side view of a number of electrically connected transducer frames in accordance with an embodiment of the disclosed technology.

FIG. 4C shows a side view of a series of aligned transducer frames 100*a*, 100*b*, 100*c*, 100*d*. Because the micro co-axial cables or the flex circuit joining the frames are flexible, the arrangement of connected transducer frames can bend and conform to a subject's anatomy such as the subject's neck if the device is to measure blood flow in the carotid artery.

In the embodiments shown in FIGS. 1A, 1B, 2A, 2B, 3A, 3B, 4A, 4B and 4C, the transducer elements are flat and are aligned to transmit and receive ultrasound signals in a direction that is normal to a face of the piezoelectric sheets. As will be appreciated by those skilled in the art, it is easier to detect fluid flow in a vessel by the measuring a Doppler shift in ultrasound signals that are transmitted and received at an angle to the fluid flow being measured. If the circuit boards described above are placed directly on a subject's anatomy, the ultrasound signals will be primarily transmitted and received in a direction that is nearly orthogonal to the fluid flow in the vessel.

Figure 5A:
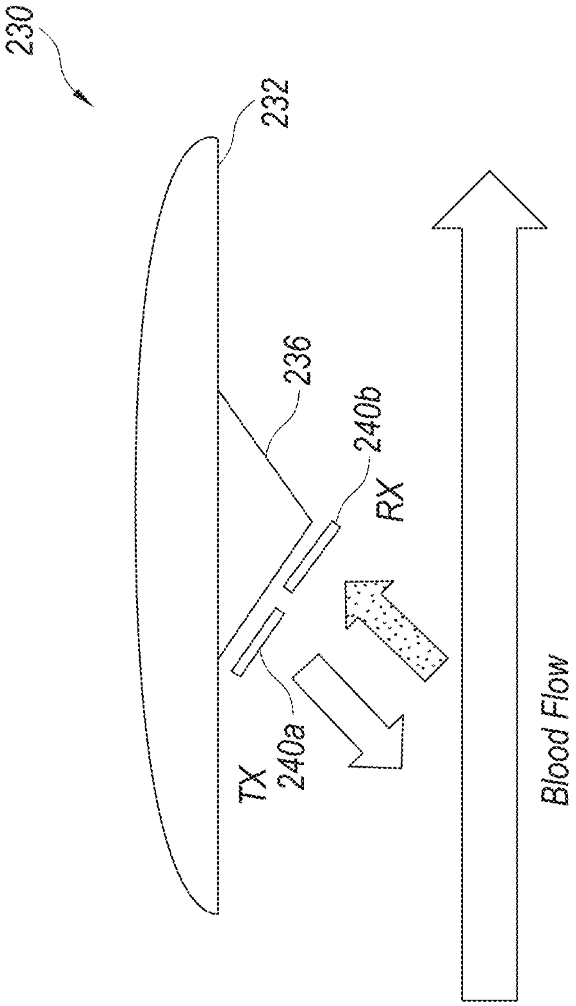
FIGS. 5A-5F show several different embodiments of a patient pad for a transducer that includes a ramp that sets an angle of the transducer elements in accordance with embodiments of the disclosed technology.

To steer the signals in a direction that is not orthogonal to the fluid flow, the circuit boards can be tilted at an angle to the vessel using a molded patient pad 230 as shown in FIG. 5A. The patient pad 230 includes a lower skin contacting portion 232 on a bottom surface. The bottom surface of the patient pad 230 includes a ramp 236 that holds the transducer elements at an angle with respect to a direction normal to the skin surface or the bottom of the patient pad. In one embodiment, the ramp is sized to fit in a notch in a subject's neck near the carotid artery and jugular vein as will be explained in further detail below.

In one embodiment, the ramp 236 is shaped to set a transmit/receive direction in a range from about 20-60 degrees (and preferably 30 degrees) with respect to the direction of flow in a vessel. In the embodiment shown, the direction of the transmit and receive elements 240*a*, 240*b* are set by the ramp 236 at the same angle with respect to the subject. In other embodiments, the transmit and receive elements may have separate ramps that are oriented at different angles to normal (or separate angles on the same ramp) so that the transmit and receive beam directions can be tailored as desired.

Figure 5B:
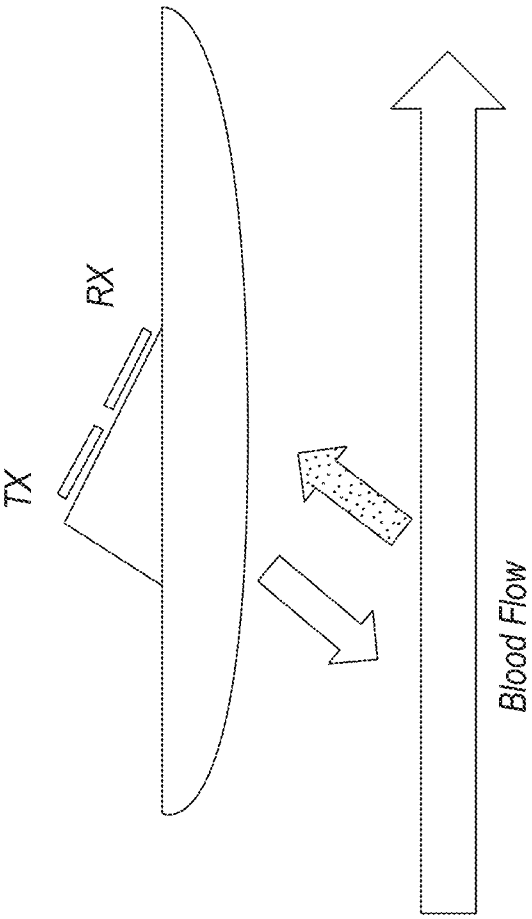

In some embodiments, the ramp 236 is not located on the front surface of the patient pad. FIG. 5B shows an embodiment where the transducers are positioned behind (e.g. proximal to) the front surface of the patient pad 230 and are oriented in a desired direction with a ramp formed 238 on the rear/proximal surface of the patient pad. The ramp 238 is angled with respect to the front or distal surface of the patient pad such that ultrasound signals are transmitted and received in a direction that is not orthogonal to the direction of fluid flowing in a vessel of interest. In this embodiment, signals are transmitted and received through the elastomeric material that makes up the patient pad and the ramp. Therefore, the elastomeric material used for the patient pad and ramp should be made of a material that is relatively transparent to ultrasound at the frequency of operation.

Figure 5C:
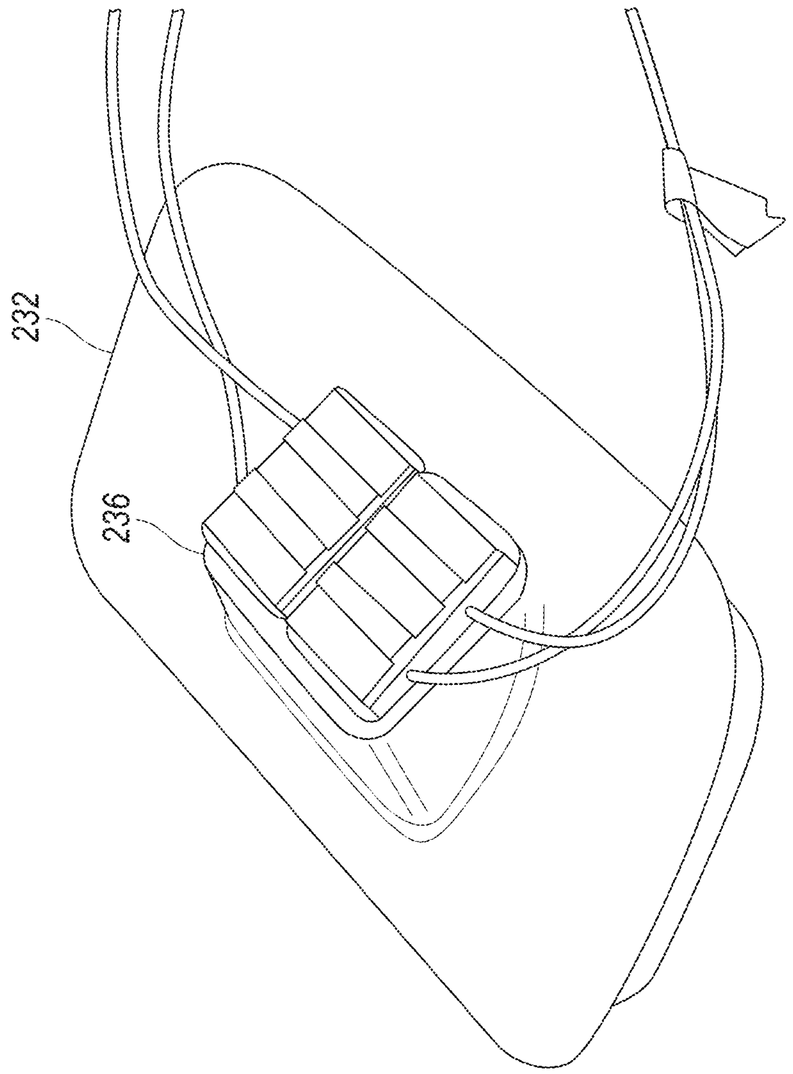

FIG. 5C illustrates a transducer where a pair of transmit/receive elements are set in a molded patient pad of the type described in connection with FIG. 5A. In the embodiment shown, two sets of TX/RX transducers are positioned on the ramp 236 to increase the width of the transmitted and received beams. The ramp 236 is sized in height and width to push the transducers into a notch or recess in the subject's neck below the jaw and to the side of the trachea in a manner that the transducers are closer to the carotid and jugular vessels. In the embodiment shown, each transducer is driven by a separate set of cables. However, the transducer elements could be wired in parallel or attached to a flex circuit as described above.

Figure 5E:
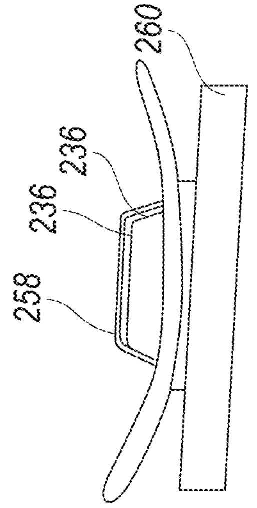
Figure 5D:
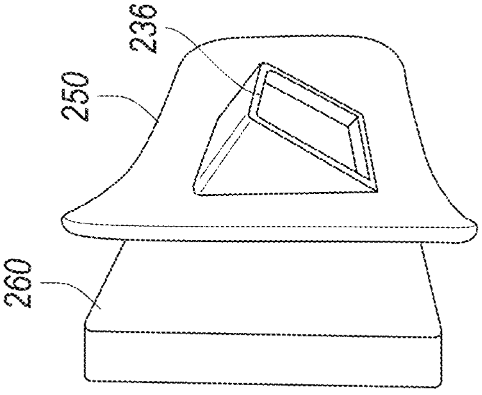

FIGS. 5D and 5E show another embodiment of a transducer in accordance with the disclosed technology. In this embodiment, an ultrasound patch has a patient pad 250 formed of a flexible elastomeric sheet (molded silicone, impregnated fabric or the like) that conforms to the subject's anatomy. A rigid housing 260 is secured behind the patient pad 250 and contains the battery, electronics and speaker etc. that generate the ultrasound signals, detect a Doppler shift in a vessel and produce an output indicative of the Doppler shift as well as transmit the signal data to a remote device.

As can be seen in FIG. 5E, the ends of the elastomeric sheet 250 can flex away from the housing 260 to conform to a subject's anatomy.

The front face of the patient pad 250 includes a ramp 236 that is molded thereon and that supports the TX/RX transducer elements at an angle (e.g. between 20 and 60 degrees) with respect to the front face of the patient pad. The ramp includes a recess 252 into which a circuit board of the type shown in FIGS. 1A and 1B can be fitted. Holes 258 within the recess 252 extend through the ramp and the patient pad to allow micro-coaxial wires or other conductors to reach the transducer elements through the body of the ramp. In some embodiments, the ramp 236 is wide enough to support two or more pairs of transducer elements side by side. In other embodiments, the ramp 236 is sized to hold a single pair of TX and RX transducer elements. In the embodiment shown, the ramp 236 is sized to allow the transducer elements to fit within a notch between the sternocleidomastoid muscle and the trachea to be closer to the carotid artery and the jugular vein of the subject.

Figure 5F:
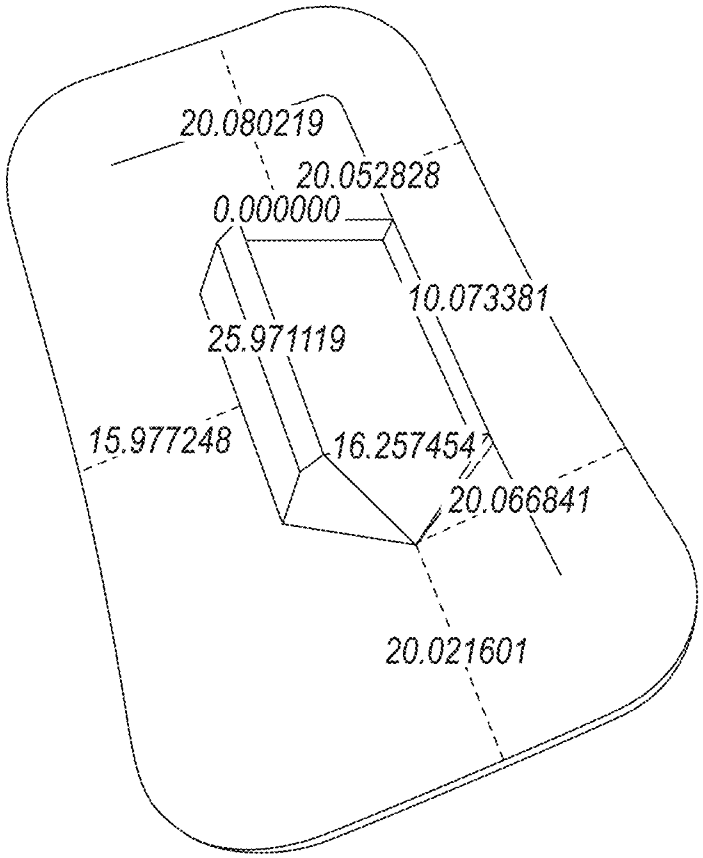

FIG. 5F provides computer-aided design (CAD) measurements of a patient pad including a ramp to support transducer elements at 30 degrees in accordance with one embodiment of the disclosed technology. The 30-degree angle is selected to create a Doppler shift angle of between 45 and 60 degrees with respect to the carotid and jugular vessels in most subjects depending on their anatomy. The patient pad is preferably made of a compliant material such as molded silicon while the transducer elements are mounted on rigid printed circuit boards to allow them to be pointed towards the carotid and jugular vessels. The placement of the ramp on the surface of the patient pad is symmetric so that the pad can be placed on either side of the subject's neck. In one embodiment, the ramp is offset along the short dimension of the patient pad to provide an indication of which way round the transducer should be oriented on the subject's neck. As can be seen, the ramp is closer to one edge of the patient pad than the other while being symmetrically placed between ends on the long dimension of the patient pad so that the transducer can be positioned on either side of the neck.

In some embodiments, the transducer elements 240*a*, 240*b* can be oriented so they lie parallel with respect to the skin surface of the subject and a lens used to steer the signals transmitted from and received by the transducer elements in a direction away from normal due to the slight delay or advancement caused by the sound waves travelling through the thicker part of the lens depending on the lens material.

Figures 6A, 6B:
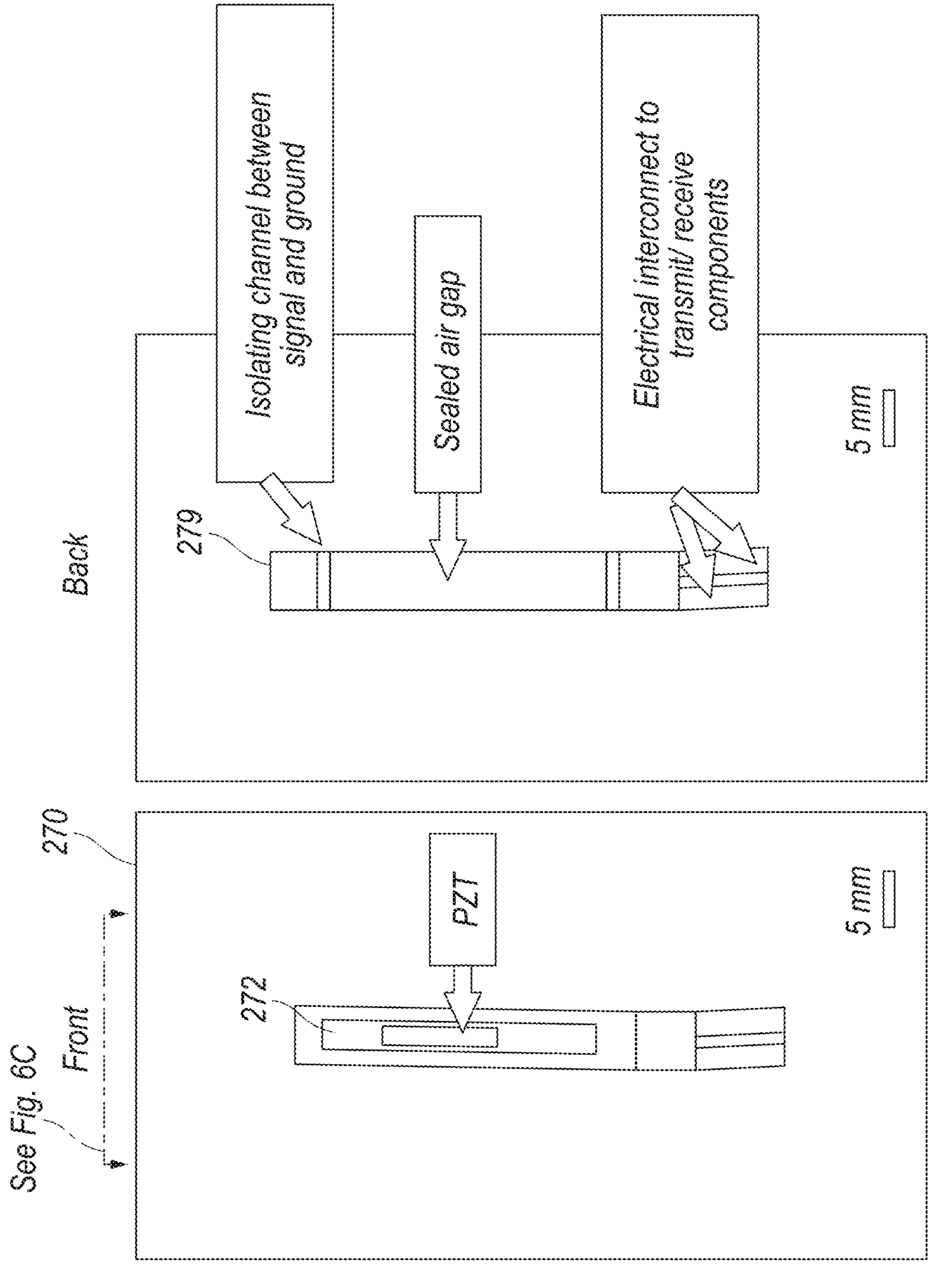

FIGS. 6A-6J show an embodiment of an air-backed ultrasound transducer 270 that can be made in batches in accordance with some embodiments of the disclosed technology. FIG. 6A shows the front or distal side 272 of a transducer and FIG. 6B shows the rear or proximal side 274 of the transducer. In some embodiments, the transducer comprises a sandwich structure of a first layer, a middle layer and a second layer where the middle layer has an aperture therein that lies behind the transducer element to form an air gap that is sealed by the second layer. In one embodiment the first and second layers are made of printed circuit board (PCB) material such as FR-4 and the middle layer is a layer of flex circuit. However, other materials could be used. The flex circuit extends outwardly from the PCB layers to provide a flexible connection to the front and rear surfaces of a piezoelectric transducer element. An airgap behind the transducer element provides an acoustic impedance mismatch to prevent/limit the rearward transmission of the ultrasound signals and reflect signals forward to increase transmission power of transducer. The depth of the airgap behind the transducer should be selected such that the glue used for the top PCB layer isn't drawn into the airgap by capillary forces.

Figure 6C:
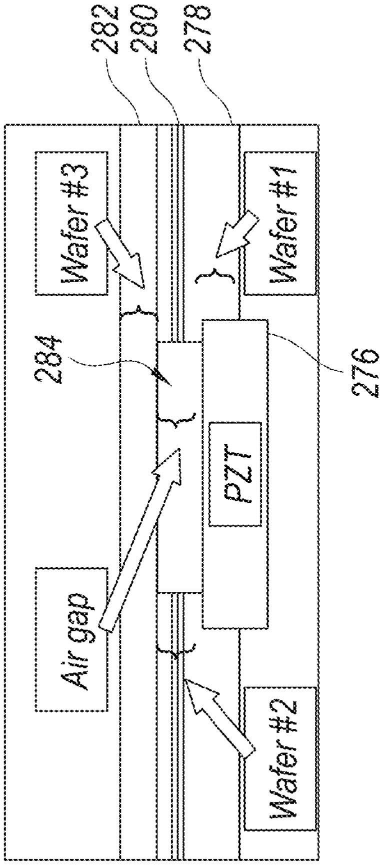

FIG. 6C is cross-sectional end view of a transducer in accordance with some embodiments of the disclosed technology. The transducer 270 includes a rectangular sheet of piezoelectric material, such as PZT, that is seated within a corresponding slot, aperture or cutout in a first layer 278 of PCB material such as FR 4. A second layer 280 of flex circuit material is behind (proximal) to the first layer 278. The flex circuit includes a slot or aperture over a portion of the PZT sheet to form an airgap 284 that is behind the PZT material. A third layer of PCB material such as FR-4 overlays the second layer 280 of flex circuit layer material to seal the airgap 284.

Figure 6D:
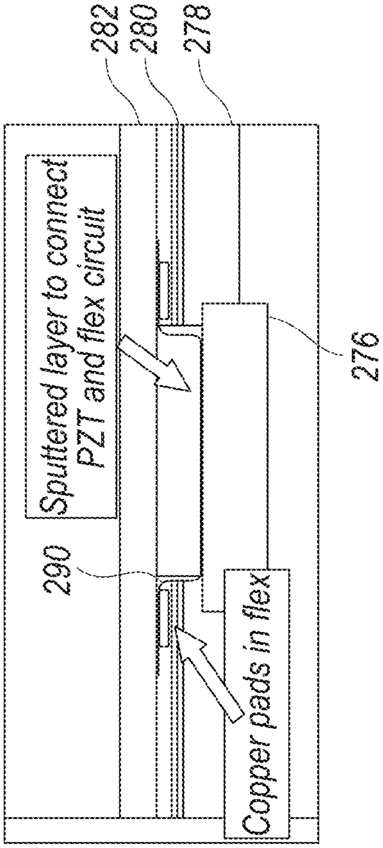

FIG. 6D is a cross-sectional view of the transducer and shows how an electrode layer is sputter coated from the flex circuit to the rear or proximal side of the PZT sheet 276 to provide an electrical contact to the PZT material. The third layer 282 is placed over the flex circuit layer after the sputter coating to seal the electrical connection under the third layer and to cover/seal the airgap 284.

Figure 6E:
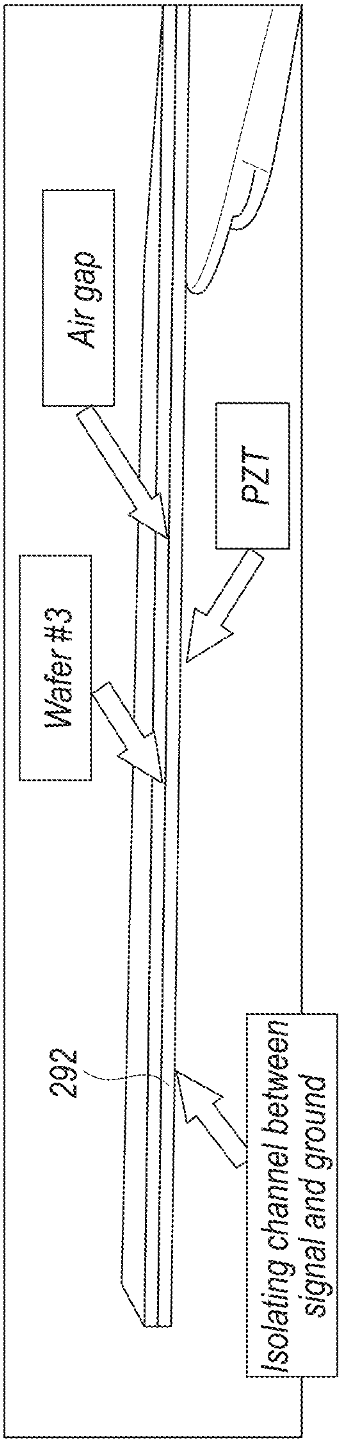

FIG. 6E is a side view of a long edge of a transducer in accordance with some embodiments of the technology. In the embodiment shown, the top and bottom surfaces of the PZT element is coated with a metal conductor such as gold or gold plus chromium via a sputtering or other deposition process. Other conductive metals such as copper or aluminum etc. could also be used. The PZT sheet is plated on both flat sides and then tilted and plated on one edge so that there is a continuous electrical path from the front surface to the rear surface via the plated edge. The PZT sheet also includes a slot or channel 292 cut on the top or bottom surface with a dicing saw or laser to break the electrical connection on one of the top or bottom surfaces so that an electrical connection can be made to both the top and bottom surfaces of the PZT element from the same side. In other embodiments, the slot or channel 292 could be made by masking a channel feature when the PZT sheet is sputter coated or screen printed etc.

Figure 6F:
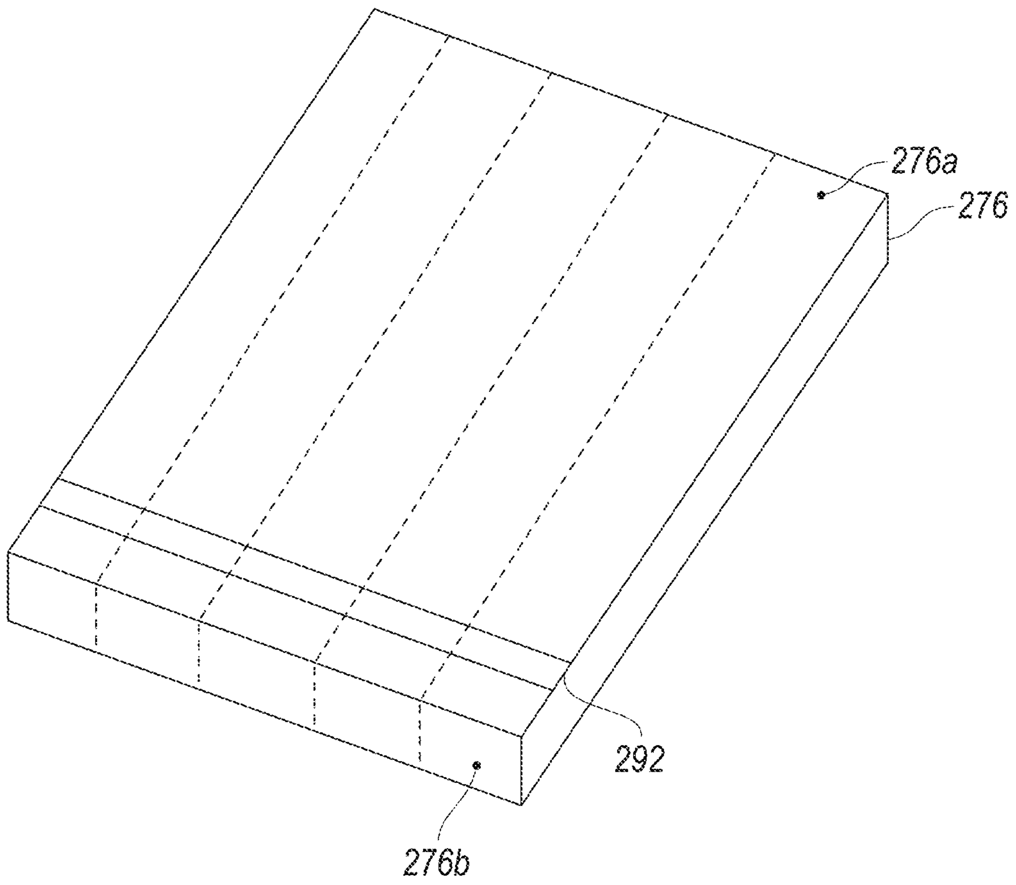

FIG. 6F shows a sheet of PZT material 276 that is plated on a top surface 276*a*, a side edge 276*b* and a bottom surface (not shown). The slot 292 breaks the electrical connection between the top surface 276*a* and the bottom surface via the plating on the edge. The sheet can be cut lengthwise along the dotted lines with a dicing saw or a patterning laser to form a number of individual PZT transducer elements.

Figure 6H:
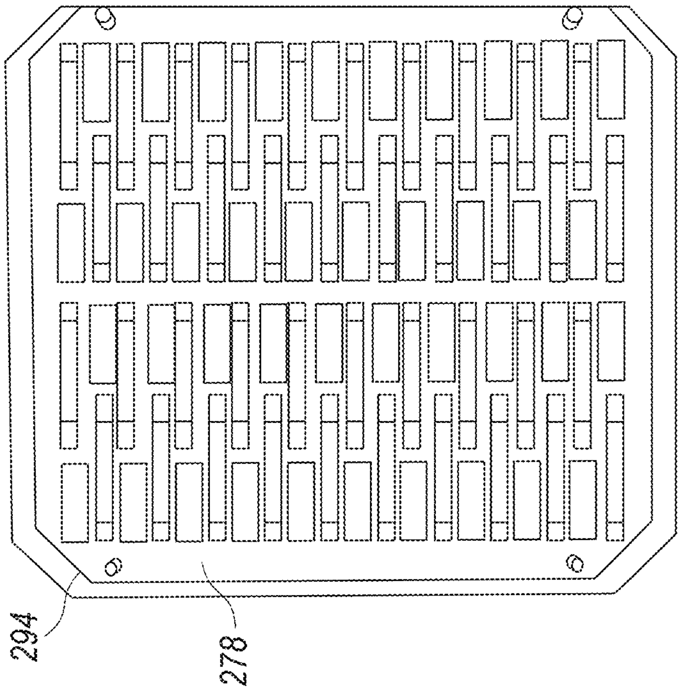
Figure 6G:
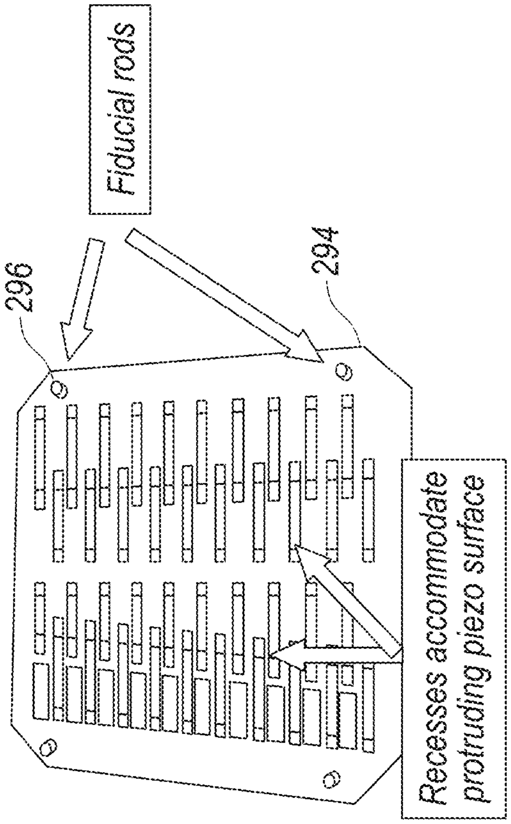
Figure 61:
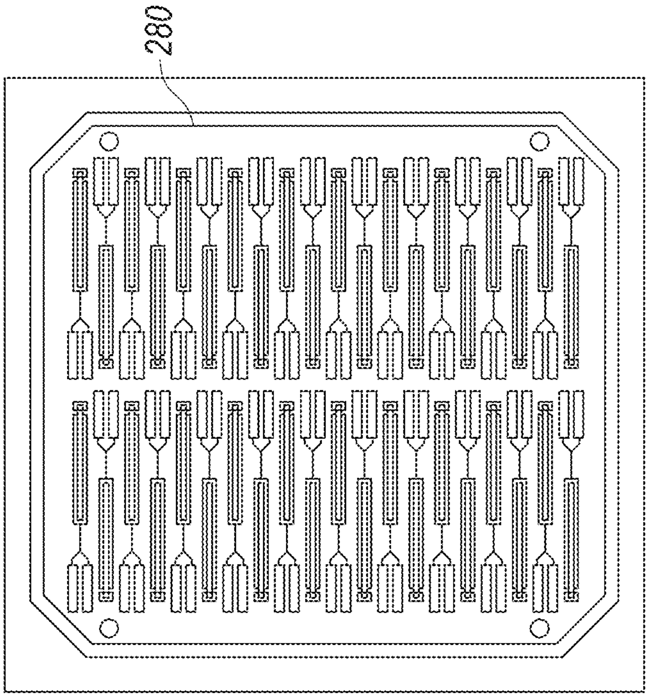
Figure 6K:
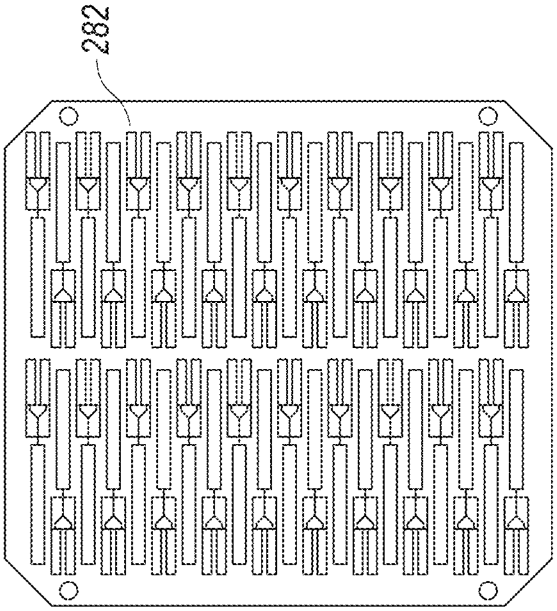

FIGS. 6G-6K show a number of manufacturing steps that can be used to make a number of electrodes in a batch process. FIG. 6G shows an assembly jig 294 that includes a number of rectangular recesses into which plated PZT elements are placed. Fiducial rods or pins 296 are placed on opposite corners of the jig to align the various layers and masks used in the manufacturing process. The jig is preferably made of a silicone impregnated plastic material that acts as a release. However, it may be useful to place a sheet of plastic wrap over the jig 294 before placing the transducer elements into the jig to prevent the transducer elements from becoming stuck in the jig.

FIG. 6H shows a sheet of the first PCB layer 278 placed over the transducer elements in the jig 294. Alternatively, the first PCB layer can be secured to the jig and the PZT elements placed into the cutouts of the first layer. The first PCB layer 287 has as number of routed slots into which the PZT elements are fitted. The recesses in the jig 294 are dimensioned such that top of PZT elements and the top surface of the first PCB layer 278 are co-planer when the PZT elements are seated in the recesses of the jig.

The next step is to glue a flex layer 280 to the first PCB layer 278 as shown in FIG. 6I. The flex layer has circuit traces formed therein and includes elongated slots or apertures that are positioned to align with a portion of the PZT elements. The dimensions of the slots/apertures in the flex layer define the dimensions of the airgaps to be formed behind the PZT elements. The dimensions of the slots in the flex layer are slightly smaller than the size of the PZT elements so that the edges of the slots lie over the back the PZT elements and can be secured to the PZT elements with an adhesive. In one technique the glue is applied to the surface of the flex layer with a roller or the like (and the second PCB layer) in order to get a thin, even layer of glue and to avoid covering the electrodes on the PZT with glue and would interfere with creating an electrical connection to the PZT as described below. The assembly jig allows firm pressure to be applied evenly across the entire stack while the adhesive is curing. This helps ensure flatness, good adhesion and good sealing of the air gap.

The next step is to place a mask (not shown) over the flex circuit layer to shield the slots in the PZT elements and the traces on the flex circuit from a sputtering process. The sputtering process forms a conductive path from traces surrounding the slots in the flex circuit layer to the plated transducer elements. As an alternative to creating the conductive path with sputtering, the conductive path could be made with conductive ink or a conductive epoxy.

Figure 6J:
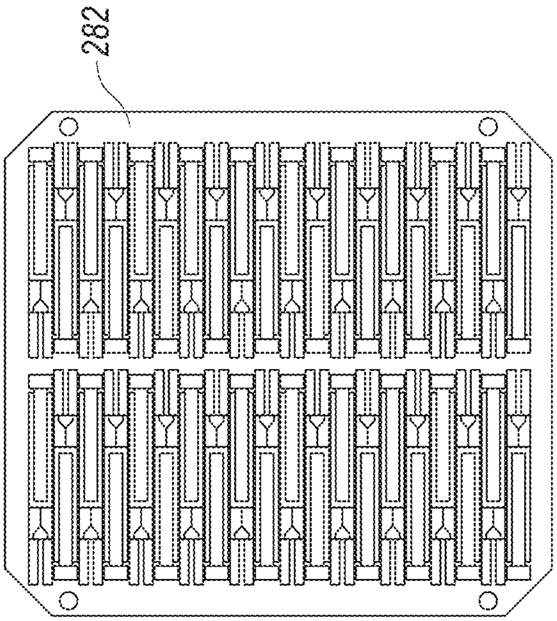

After the traces in the flex circuit are electrically connected to the transducer elements, the top PCB layer 282 is glued to the flex circuit layer as shown in FIG. 6J. The top PCB layer 282 covers the slots/apertures in the flex circuit thereby sealing the airgaps behind each transducer element. After the third PCB layer 282 is glued to the flex layer 280, the transducer elements can be separated from the jig and sawn to create individual transducers. The front face of the batch of transducers can be seen in FIG. 6K.

Figure 6N:
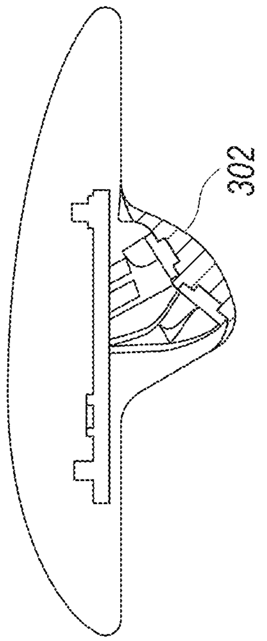
FIGS. 6L-6N show a number of different lenses that can be secured to the front of a transducer in accordance with some embodiments of the disclosed technology.
Figure 6L:
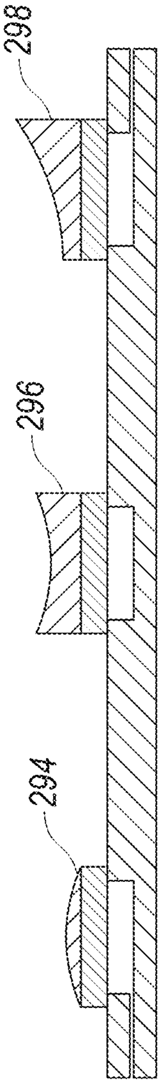

Individual transducer elements can be fitted with a lens as shown in FIG. 6L. Lens elements having different shapes such as convex 294, concave 296 or tilted concave 298 can be secured via an adhesive to the front surface of the PZT elements to focus the beam from the transducer elements. In other embodiments, the lens material could be cast directly onto the surface rather than being applied with a separate adhesive. Such lenses can be made of silicone rubber or other materials depending on the type of focusing desired.

Figure 6M:
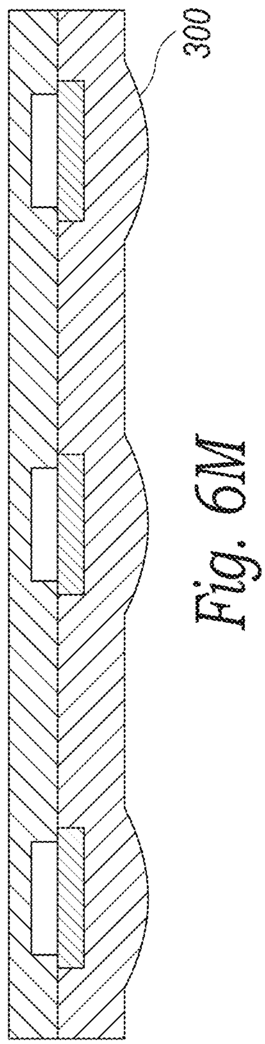

FIG. 6M shows an embodiment where a protective layer 300 including molded lens elements is placed over a number of adjacent transducer elements. The protective layer 300 covers the spaces between the transducer elements and the lenses are positioned in front of the transducer elements. The protective layer 300 can cushion the transducer from shocks or drops while the lens elements focuses the ultrasound in a desired direction.

FIG. 6N shows an example of a lens 302 that is over molded onto a pair of transducer elements that are set on a ramp as discussed above. As indicated above, in some embodiments, the ramp for the transmit element may have a different angle compared with the angle of the ramp for the receive element so that the focus area for the transducer elements overlap in an area of interest. The lens 302 is molded over the front surface of the transducer elements to focus the ultrasound in a desired direction and can serve to protect the exposed PZT elements.

Figure 6P:
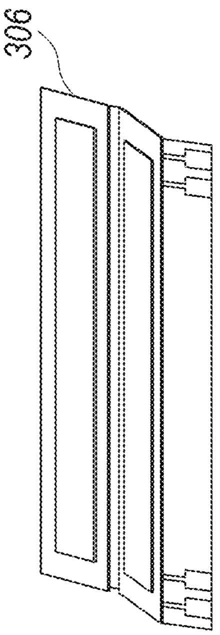
FIGS. 6O-6Q show alternative air-backed transducer configurations in accordance with some embodiments of the disclosed technology.

In the embodiments shown in FIGS. 6A-6K, the air-backed transducer elements are generally singular elements. FIGS. 6O and 6P show two alternative designs where a single flex circuit is connected to a pair of transducer elements. In FIG. 6O, a flex circuit at either short end of two adjacent transducer elements joins the transducer elements so that they are hinged together. There is a gap between the flex circuits along the length of the transducer elements. FIG. 6P shows an embodiment 306 where a single flex circuit joins two transducer elements from the long side so that they are foldable with respect to one another.

Figure 6Q:
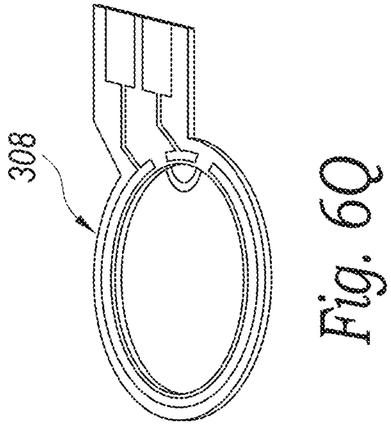
Figure 6O:
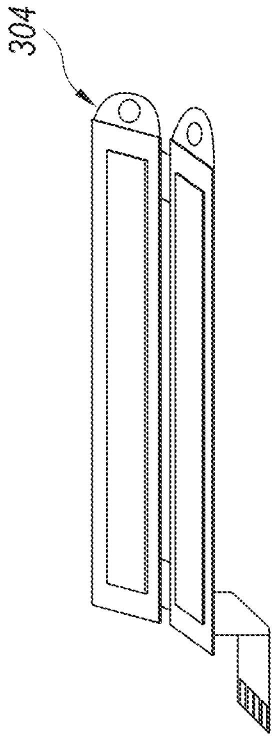

In the embodiment shown in FIG. 6Q, a transducer element 308 is round and not rectangular. The round PZT element is plated on both sides plus at least a portion of an edge. One side of the PZT transducer element includes a slot or channel to break the electrical connection from the plated first side of the PZT transducer element to the second plated side of the transducer element.

The transducer elements shown in FIGS. 6O-6P can be batch made with the same sandwich configuration described above. In the examples described above, the transducers include three layers. The first PCB layer is primarily used to position the PZT elements and provide stability. Therefore, in some embodiments, the first PCB layer could be omitted. Similarly, more than three layers could be used. In other embodiments, the flex circuit tabs used to connect the PZT elements could be replaced with surface mount connectors. Furthermore, a single flex circuit could be used to connect to multiple PZT elements similar to the embodiment shown in FIG. 4C.

Figure 7:
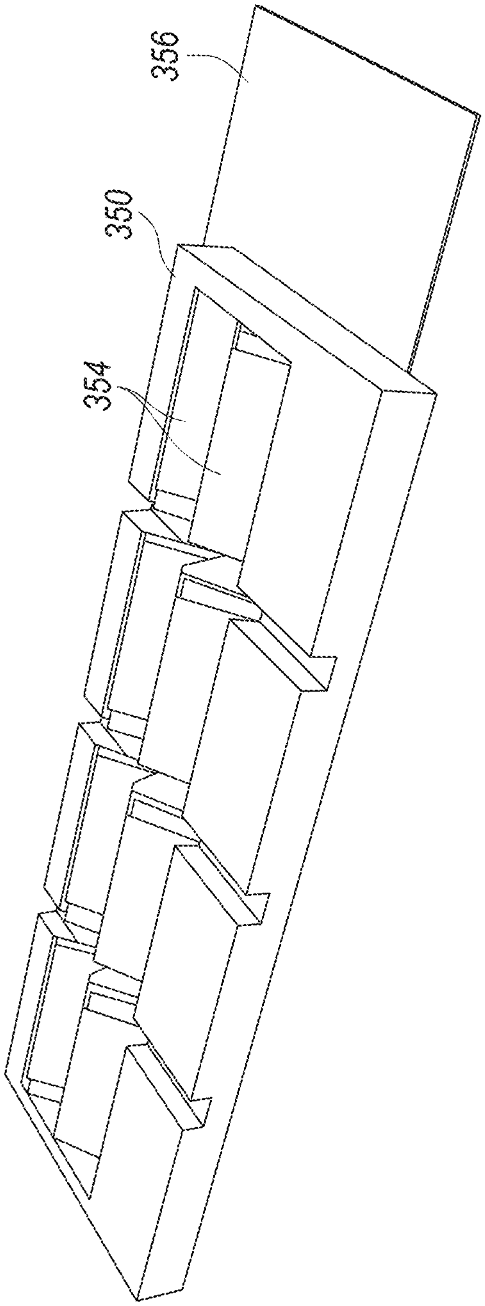
FIG. 7 shows a frame for supporting transducer elements at an angle in accordance with another embodiment of the disclosed technology.

FIG. 7 shows another alternative embodiment of a frame that supports a number of transducer pairs. In this embodiment, a frame 350 is molded or 3D printed to support a number of TX and RX transducer 354 elements at an angle to a front face of the transducer. In the embodiment shown, the frame 350 supports four TX elements and four RX elements. In one embodiment, the TX and RX transducer elements are supported by the frame 350 at an angle between 20 and 60 degrees with respect to a face of the transducer. The frame can include angled side rails in which edges of the transducer elements are fitted so that the backs of the transducer elements are open or the transducer frame can include a number of angled, acoustically transparent backing supports that support the transducer elements along their length. A printed flex circuit 356 includes conductors or traces (not shown) that connect to the front and rear surfaces of each transducer element. The frame 350 allows the rear surface of the transducer elements to be exposed (e.g. air-backed). In some embodiments, a light foam material can be placed on the rear surface of the transducer elements when they are in the frame.

In some embodiments, the frame 350 and flex circuit are encapsulated in a material that provides a good acoustic match to the tissue to be examined such an elastomer e.g. silicone or a powder-loaded silicone.

Figure 8:
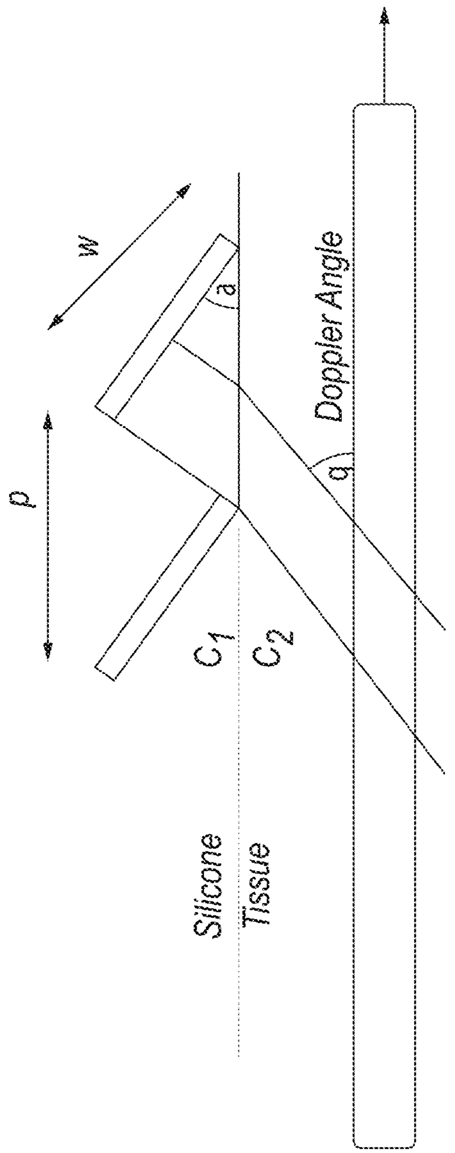
FIG. 8 shows one orientation of a pair of transmit/receive transducer elements with respect to a vessel in order to detect a Doppler shift in the ultrasound signals that are directed to the vessel.

As indicated above, the angle of the TX and RX elements is preferably set either by physically orienting the transducers in the frame or by the use of a lens or a ramp as shown in FIGS. 5A and 5B. As shown in FIG. 8, the angle $\alpha$ of the transducers is set such that the Doppler angle to the flow in a vessel is between 20 and 60 degrees. The angle $\alpha$ is selected to compensate for the change in beam direction from the Snell's law effect at the transducer/tissue boundary. The angle of the TX and RX elements need not be the same and in some embodiments, are different so that the TX and RX beams overlap in the area of the vessel.

Figure 9:
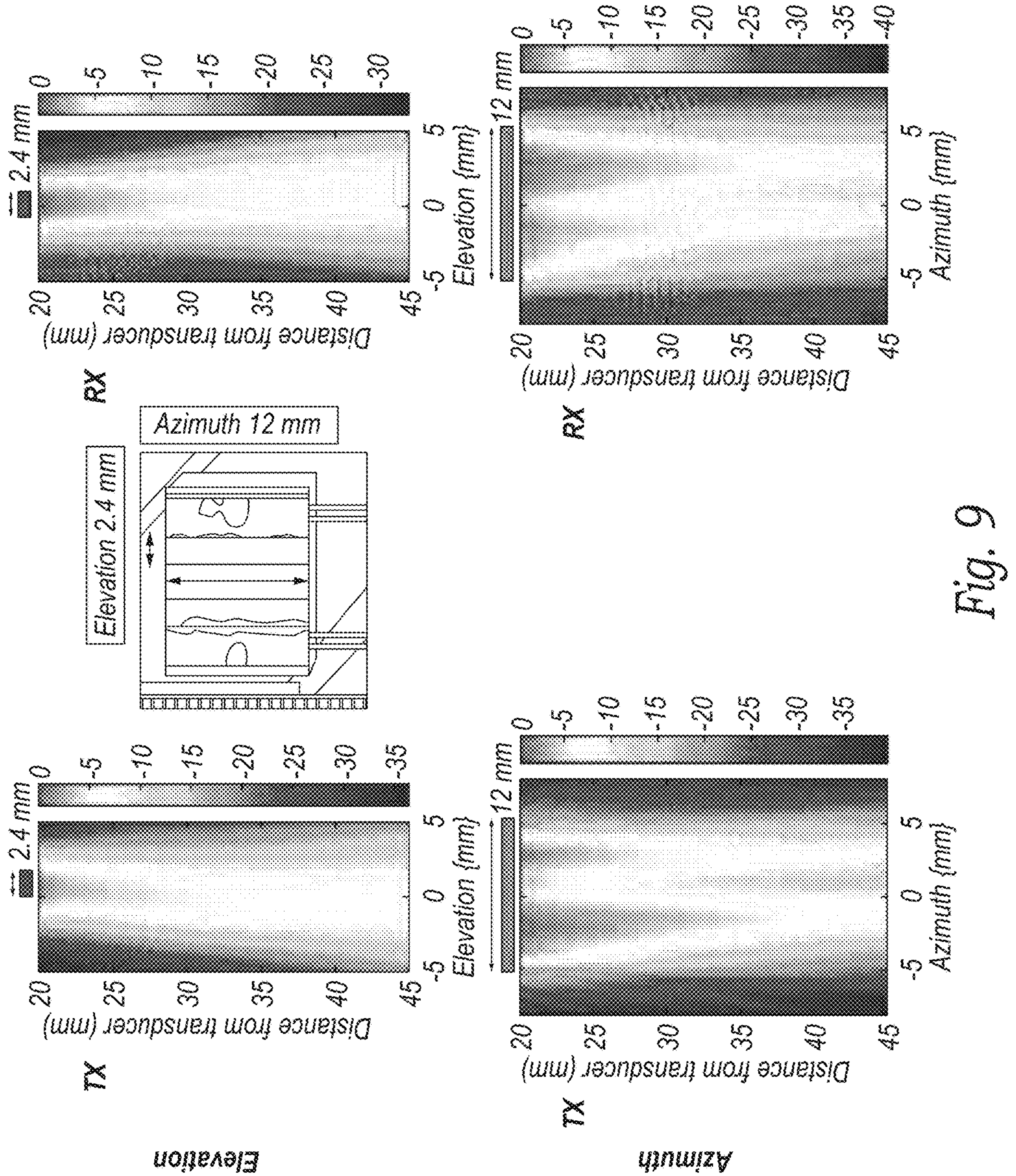
FIG. 9 shows a number of measured beam plots for a transducer constructed in accordance with one embodiment of the disclosed technology.

FIG. 9 shows sample beam plots for air-backed TX and RX elements with an element size of 2.4 mm. in elevation and 12 mm. in the azimuthal direction when operated at a center frequency of 4 MHz. The beam pattern has a generally flat sheet-like shape of approximately 1 cm. thick out to a distance of 45 mm. from the transducer and a nearly uniform power across the face of the transducer to at least 30 mm. from the transducer. In one embodiment, several TX/RX transducer pairs are aligned side by side so that the flat planes of ultrasound transducers will intersect the subject's vessel regardless of variations in placement by the operator. If wired separately, the TX/RX pair producing the best signals for a vessel of interest can be selected to produce the signals that are analyzed to estimate flow in the vessel.

Figure 10B:
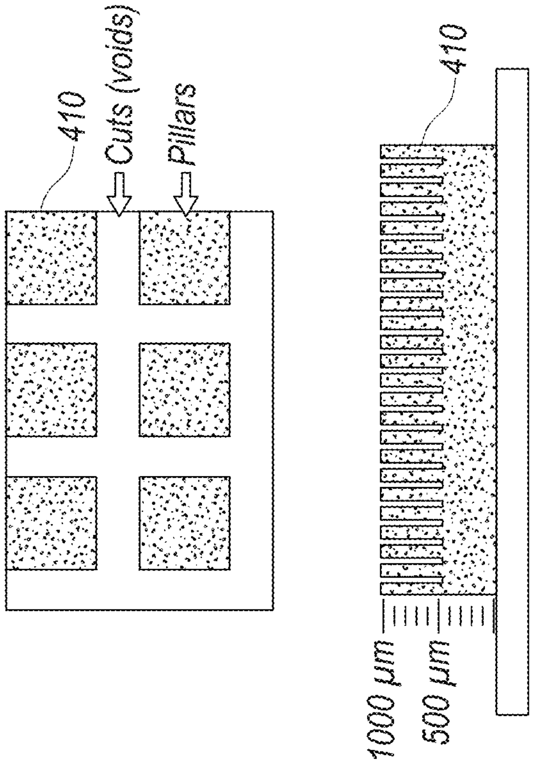
FIGS. 10A-10Q illustrate a number of manufacturing steps to fabricate a flexible phased array transducer in accordance with some embodiments of the disclosed technology.
Figure 10A:
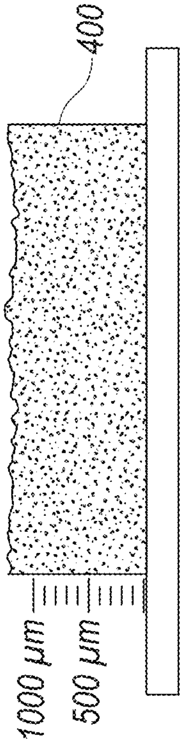
Figure 10D:
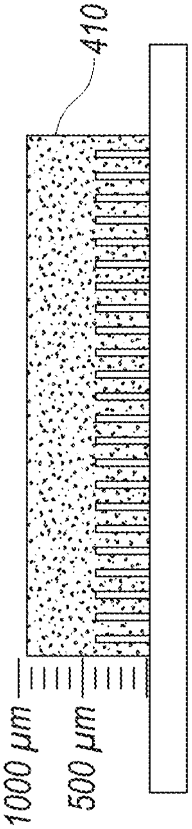
Figure 10F:
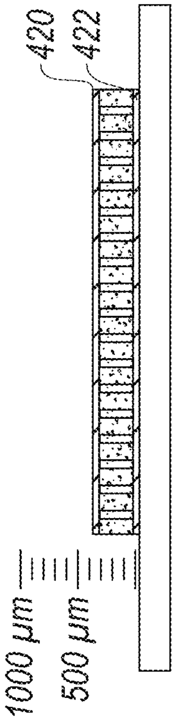

In some embodiments, steering the transmit and receive beams is accomplished with a flexible phased array transducer instead of physically orienting the transducer elements at an angle. FIGS. 10A-10Q show a number of manufacturing steps employed to make a flexible phased array transducer that can be driven to steer the beam at a desired angle with respect to the surface of a subject's skin in order to detect Doppler signals from a vessel. The phased array disclosed is useful for measuring flow at locations where the skin is relatively flat such as on the wrist, ankle or thigh where the ramp design described above may be uncomfortable to wear for long periods of time.

In one embodiment, the flexible phased array transducer is manufactured from a sheet of piezoelectric material 400 such as PZT or other known piezoelectric material. In one embodiment shown in FIG. 10A, the sheet 400 starts with a thickness greater than the resonant mode thickness. The sheet 400 is lapped or ground to a desired thickness (e.g. about 1000 um) and is diced with a saw or patterning laser to create a number of square pillars 410 as shown in FIG. 10B. In one embodiment, for a 4 MHz transducer, the pillars are about 125 um on each side and are separated by 60 um kerf cuts. The pillars are about 500 um in height. However, other sizes could be used depending on the frequencies to be used. In addition, other shapes besides square pillars could be used such as triangles, pentagons, hexagons, rectangles etc. Having a large number of small pillars in the transducer allows the transducer to flex as will be described below.

Figure 10C:
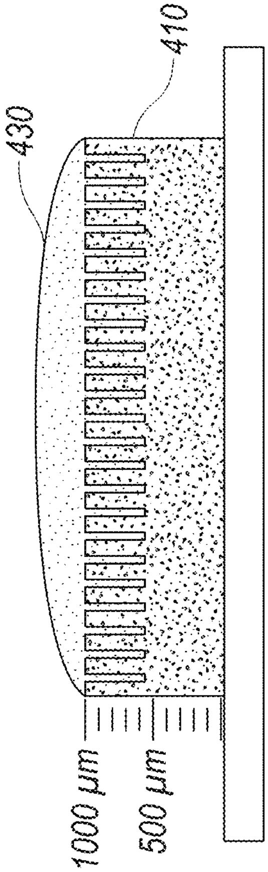
Figure 10E:
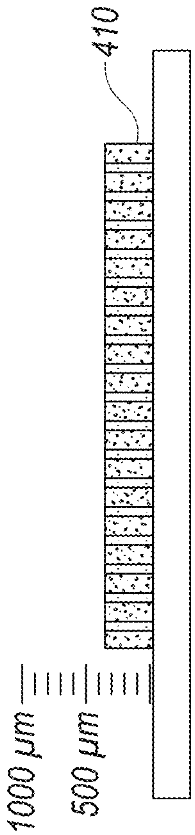
Figure 10H:
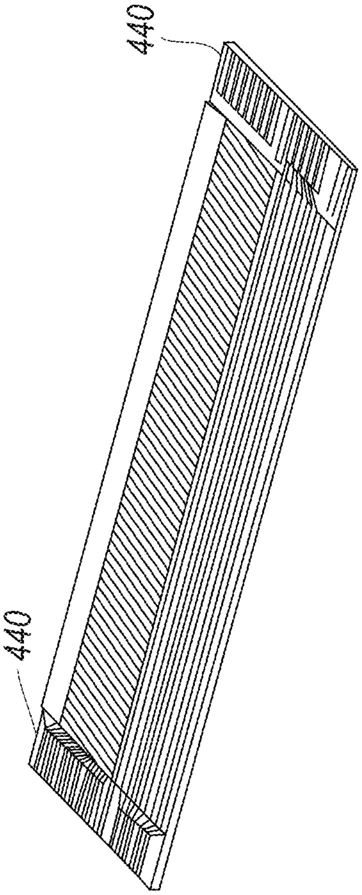

The pattern of pillars 410 is then coated with a flexible adhesive such as a flexible epoxy 430 in a manner that avoids trapping air bubbles between the pillars (e.g. under vacuum) as shown in FIG. 10C. Once the pillars are filled and the adhesive has cured, the substrate is lapped or ground on both sides to a desired thickness corresponding to the piezoelectric resonance frequency (e.g. <500 um) as shown in FIGS. 10D, 10E, leaving only the pillars 410 joined by the adhesive. The result is a flexible 1-3 composite transducer.

Figure 10G:
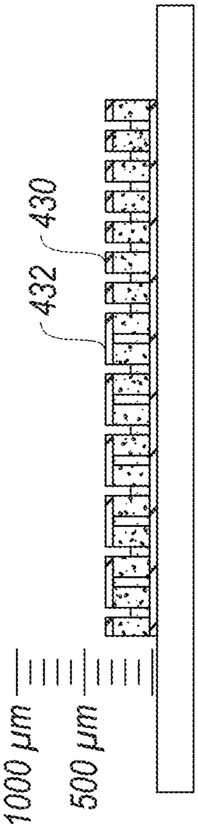

The top and bottom surfaces 420, 422 of the pillars 410 and adhesive are then coated with an electrode such as gold, copper, aluminum, or other conductive metal by sputter coating or other metal depositing technique as shown in FIG. 10F, In one embodiment, the bottom electrode is only deposited in an active area of the transducer and not over the entire surface. Individual elements for the phased array are then formed by cutting the top electrode surface into rows. Such patterning can be with a saw, a patterning laser or by using a photolithographic technique. In the embodiment shown in FIG. 10G, the transmit elements 430 are a single pillar wide so that kerf cuts or spaces in the electrode are placed between each row of pillars. In the embodiment shown, the receive elements 432 are two pillars wide so that kerf cuts are made on every other row. The transmit elements therefore consist of a single row of pillars electrically connected by a common electrode that extends along the long dimension of the transducer face. The receive elements consist of two adjacent rows of pillar elements electrically connected by a common electrode that extends along the long dimension of the transducer face. In some embodiments, the kerf cuts for the elements remove some of the adhesive between adjacent rows of pillars. In other embodiments, such as if the element patterning is done with a laser, only the top electrode is removed in between the pillars and the majority of the adhesive is left between the adjacent rows of pillars. In other embodiments, the electrodes are not aligned with pillars such as in randomized 1-3 composites, 0-3 composites and film transducers.

In addition to forming the transducer TX and RX elements, the deposited electrode metal forms fan out tabs 440 at the ends of the transducer elements to provide an electrical connection to the TX and RX elements. In one embodiment, one side of the transducer has fan out tabs for all the even numbered transmit and receive elements while the other side of the transducer has the fan out tabs for the odd numbered transmit and receive elements.

Figure 10J:
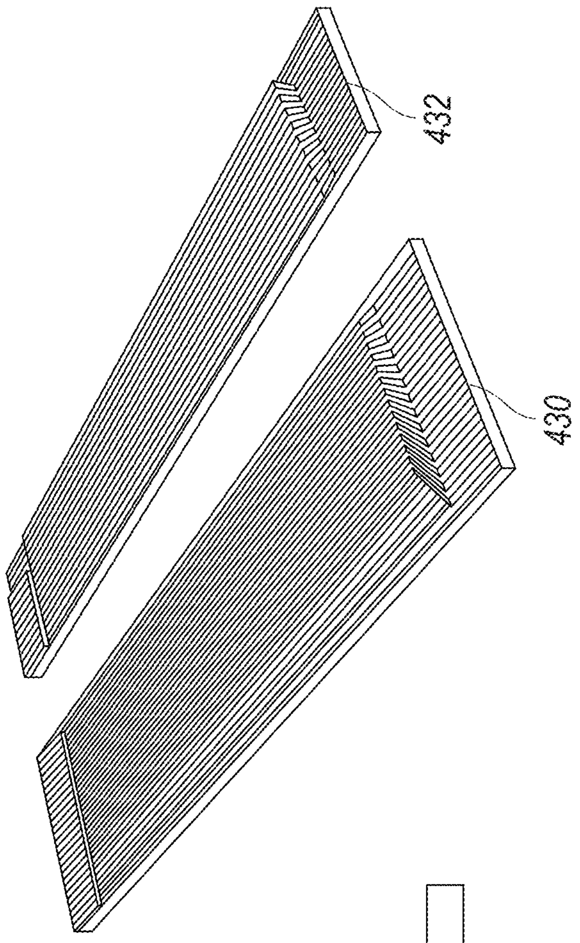
Figure 10I:
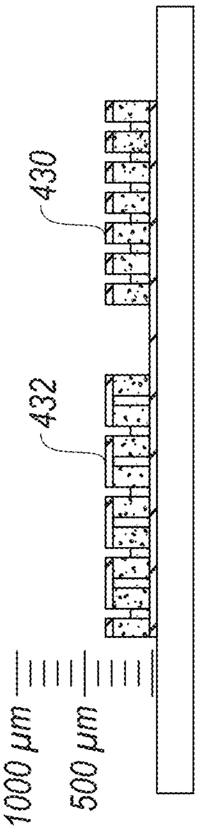
Figures 1, 10L:
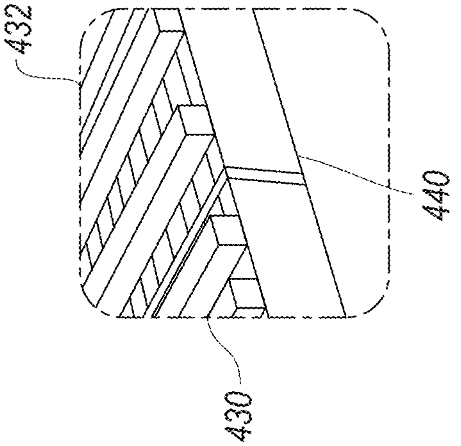
Figure 10L:
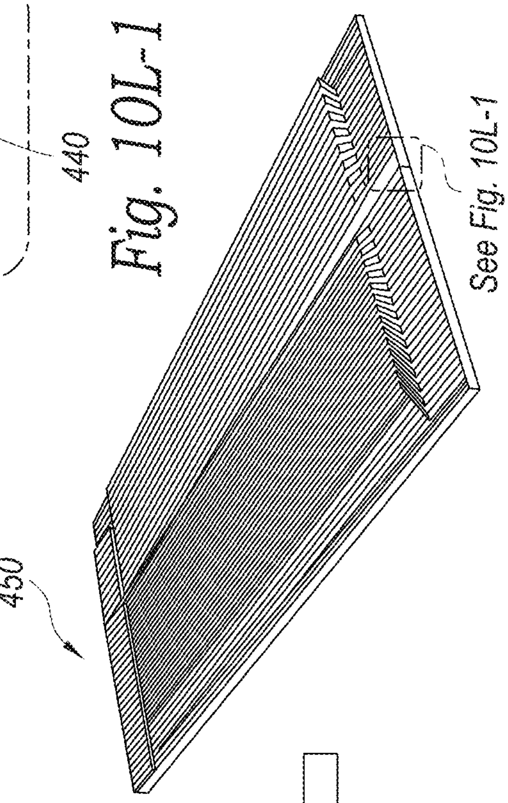
Figure 10K:
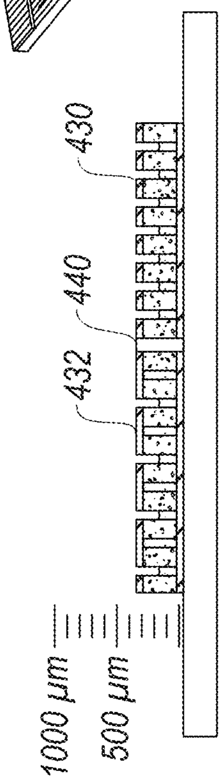

In some embodiments, to reduce cross-talk between the transmit and receive elements, the transmit elements 430 are separated from the receive elements 432 by cutting the transmit elements from the receive elements in the piezoelectric sheet 400 with a saw or laser as shown in FIGS. 101 and 10J. In some embodiments, the transmit and receive elements are then rejoined to create a completed phased array transducer 450 by placing an adhesive foam strip 440, soft epoxy, room temperature vulcanizing (RTV) or other dampening material between the sheet containing the transmit elements and the sheet containing the receive elements as shown in FIGS. 10K and 10L.

Figure 10N:
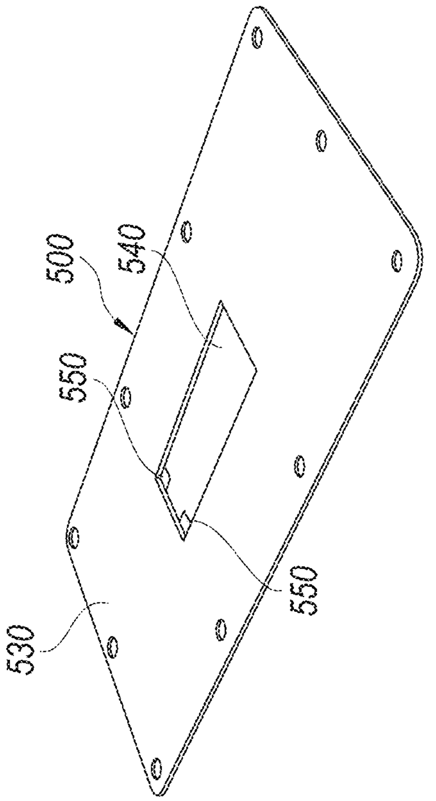
Figure 10M:
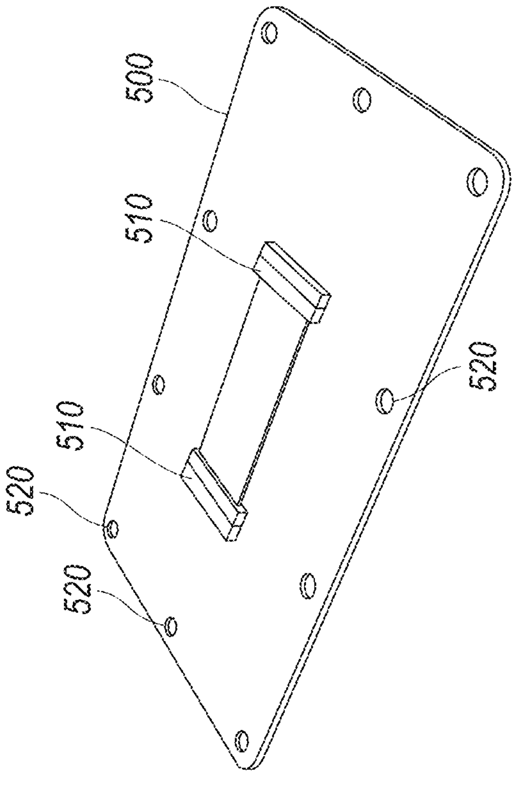

Once the transducer 450 is complete, it is mounted on a flex circuit 500 as shown in FIGS. 10M and 10N. In the embodiment shown, the flex circuit 500 includes a pair of zero insertion force (ZIFF) connectors 510 that receive the fan out tabs of the transducer to make an electrical connection to the transmit and receive elements. In some embodiments, one ZIFF connector 510 makes connections to the even numbered transmit and receive elements and the other ZIFF connector 510 makes connections to the odd numbered transmit and receive elements. In some embodiments, the transducer elements are permanently bonded to the flex circuit by soldering, wire bonding or laser-welding.

FIG. 10M shows a top surface of the flex circuit 500. The top surface of the flex circuit 500 also includes a number of traces (not shown) that are patterned to make connections to the other circuit components (not shown) to be placed on the flex circuit. In some embodiments, the flex circuit includes a number of holes 520 about its perimeter through which wires can be passed to make connections to features on the other side of the flex circuit. Alternatively, the holes 520 can be plated through or filled with a conductive material to make an electrical connection between features on the top and bottom surfaces of the flex circuit 500.

FIG. 10N shows the bottom surface of the flex circuit 500. The bottom surface 530 includes a rectangular opening 540 behind which the transducer 450 is placed. In some embodiments, all or a majority of the bottom surface 30 of the flex circuit 500 includes a common electrode that is electrically coupled to the electrode on the front face of the transducer via one or more tabs 550 on the flex circuit and a conductive adhesive. The common electrode on the bottom surface of the flex circuit can be connected to components or electrodes on the top surface of the flex circuit through a conductor passed through one or more of the holes 520, via a plating or other conductive material in the holes 520 or via a conductor (wire or foil etc.) that wraps over an edge of the flex circuit 500. As can be seen in FIG. 10N, the opening 540 exposes the bottom ground electrode surface of the transducer 450 and provides an acoustic window to allow ultrasound energy to pass through.

Figure 10P:
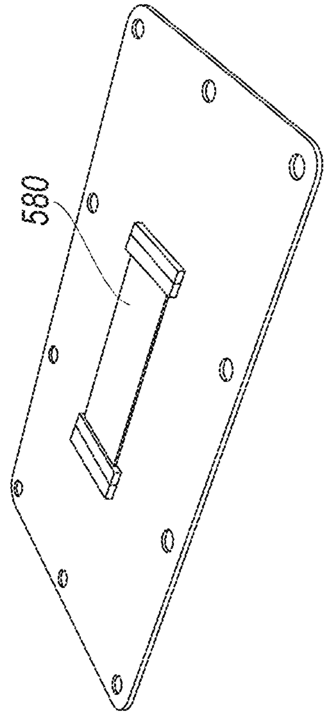
Figure 10O:
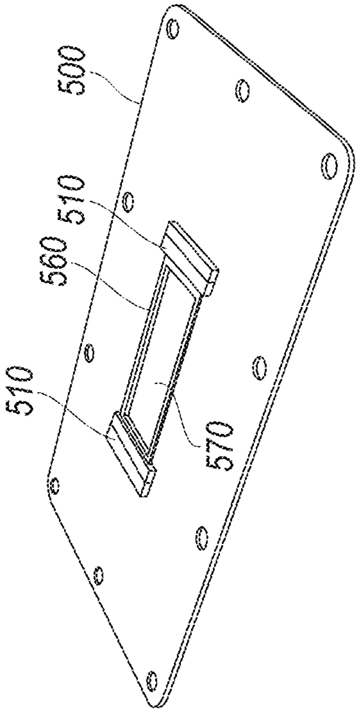
Figure 10Q:
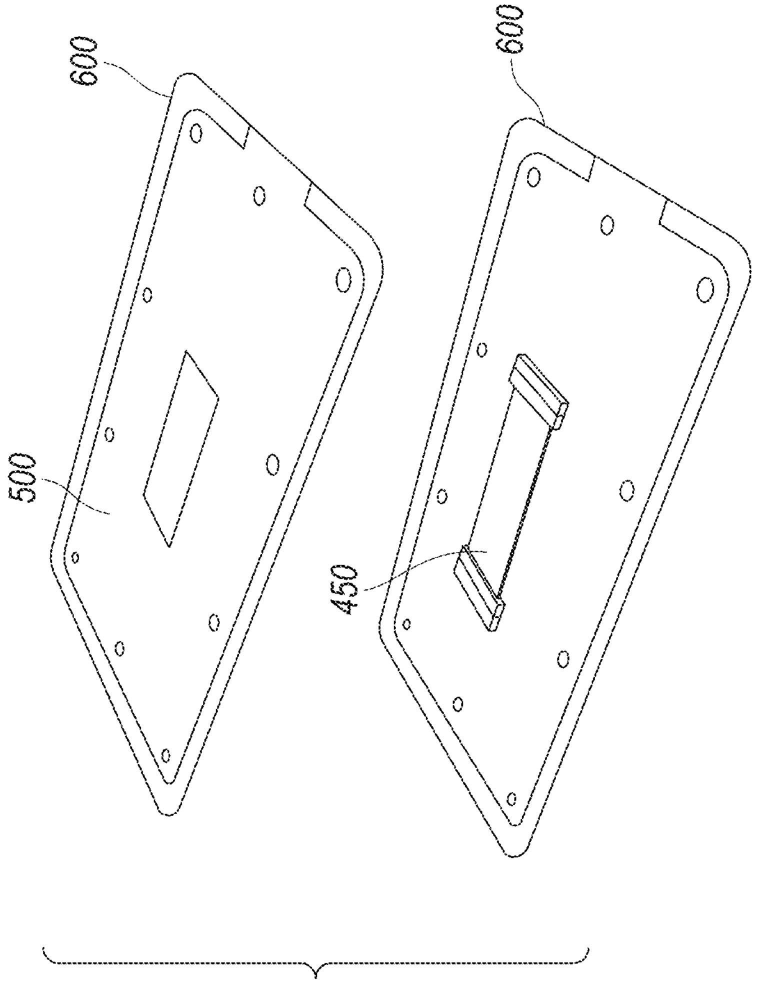

To create an air backing for the pillars of the transducer 450, a spacer 560 such as a strip of adhesive foam is placed around the perimeter of a rear surface of the transducer 450. The spacer 560 has an opening 570 positioned over the electrodes for the transmit and receive transducer elements as shown in FIG. 10O. A cover 580 is placed over the spacer 560 (FIG. 10P) to create an air gap behind the transducer elements. With the cover 580 in place, the transducer 450 and the flex circuit 500 can be placed in a mold and encapsulated in a flexible elastomeric material 600 such as silicone as shown in FIG. 10Q. Once encapsulated, ultrasound signals created by the transducer elements and the corresponding return echo signals pass through the flexible material 600.

Because the transmit and receive transducer elements are formed of a number of electrically connected, piezoelectric pillars that are joined by a flexible adhesive, the transducer 450 can bend to conform to a subject's anatomy. In some embodiments, the transducer can be made to be rigid.

Figure 11A:
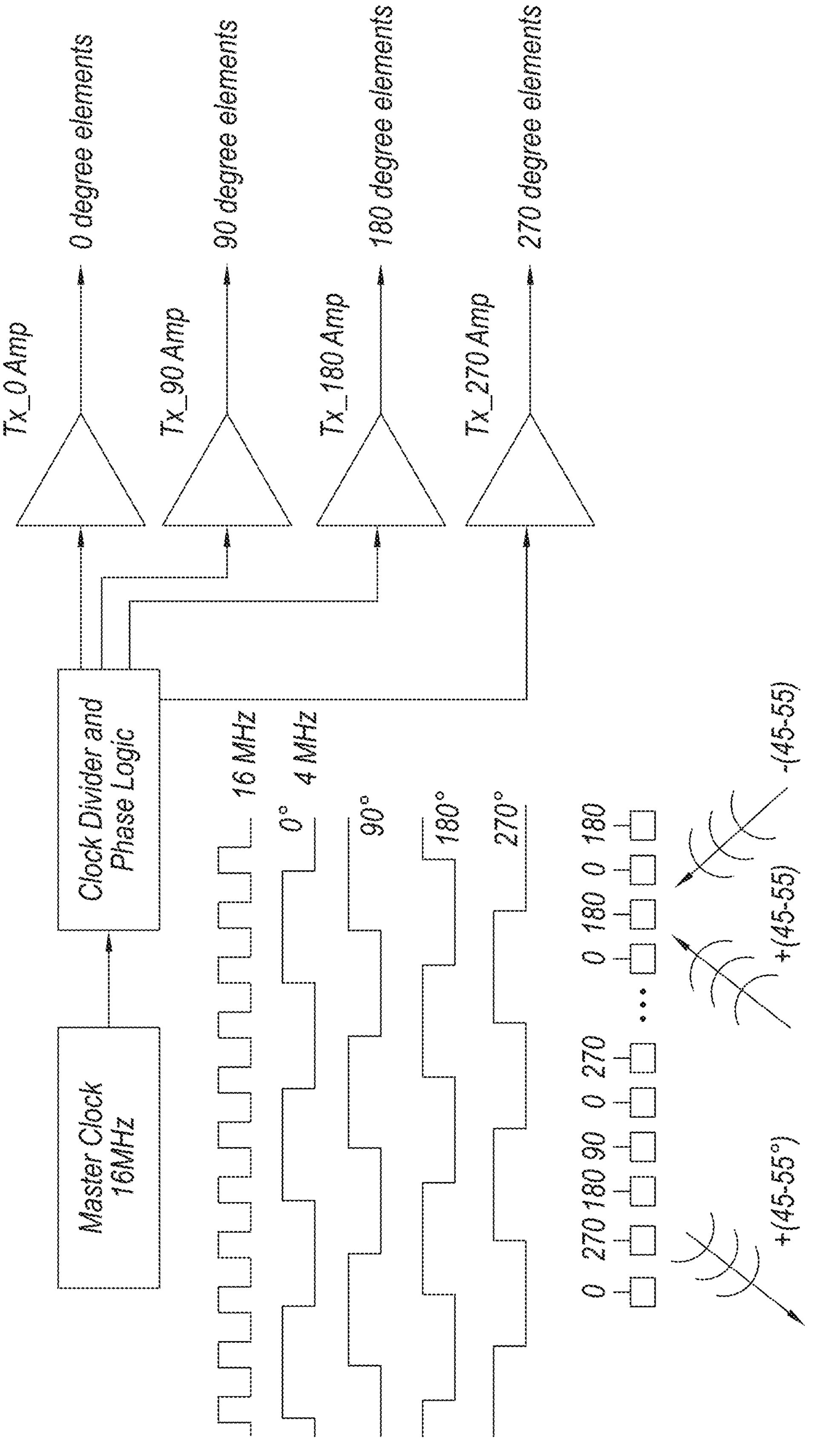
FIG. 11A is a block diagram of a portion of a transmit circuit for driving elements of a phased array transducer in accordance with some embodiments of the disclosed technology.
Figure 11B:
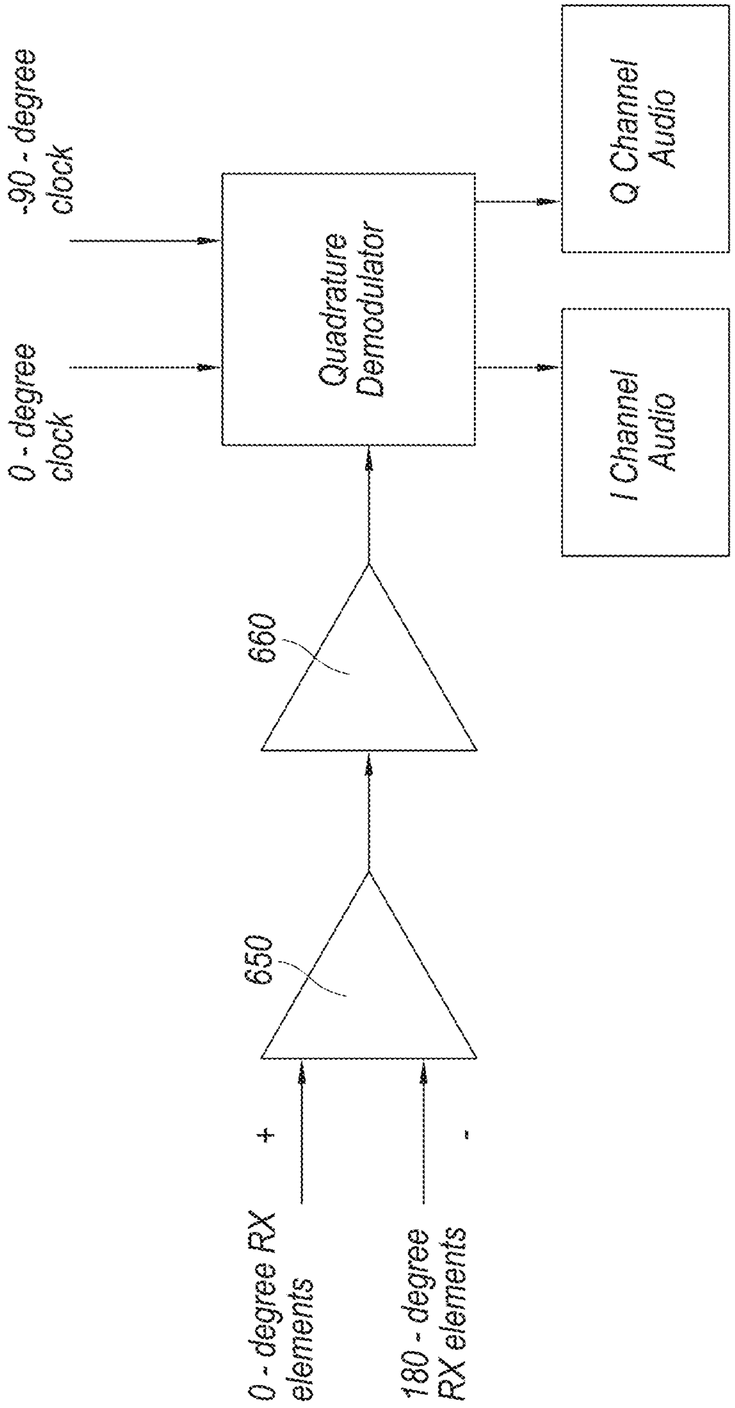
FIG. 11B is a block diagram of a portion of a receive circuit to detect Doppler signals from a phased array transducer in accordance with some embodiments of the disclosed technology.

FIGS. 11A and 11B are block diagrams of a portion of a transmit and receive circuit used to drive the flexible phased array transducer described above. In one embodiment, a clock source 600 is divided by a clock divider and phase logic circuit 610 to produce four corresponding clock signals at 0, 90, 180 and 270 degrees with respect to the input clock. In one embodiment, the clock source 600 has a frequency of 16 MHz and the divided clock signals have a frequency of 4 MHz, which is the transmit frequency of some embodiments of the ultrasound patch. In one embodiment, the clock divider and phase logic 610 is implemented with D-type flip flops in a Johnson ring counter configuration. Each of the divided clock signals is amplified by a corresponding amplifier 620*a*-620*d* and applied to the rows of the transmit elements in a repeating pattern. In one embodiment, the various phase clock signals are applied to adjacent transmit elements in the order 0, 270, 180, 90, 0, 270, 180, 90 etc. to produce a transmit angle between +45-55 degrees depending on the size and spacing of the transducer pillars and the frequency of transmission. Other orders of clock signals delays can produce other beam directions. The element-to-element pitch 'p' with this embodiment is designed according to the following formula:

$$p = \frac{\lambda}{4 \cdot \cos(\theta_D)}$$

where lambda is the wavelength of the ultrasound within the propagation medium and theta is the desired Doppler angle. In another embodiment, the various phase signals are applied to adjacent transmit elements in the order 0, 180, 0, 180 etc. to produce a transmit angles of +(45-55) and −(45-55) degrees depending on the size and spacing of the transducer pillars and the frequency of transmission. The element-to-element pitch 'p' with this embodiment is designed according to the following formula:

$$p = \frac{\lambda}{2 \cdot \cos(\theta_D)}$$

where lambda is the wavelength of the ultrasound within the propagation medium and theta is the desired Doppler angle. In one embodiment, pairs of receive elements in the transducer selectively receive ultrasound energy at angles of +(45-55) and −(45-55) degrees depending on the size and spacing of the elements when the two signals are processed as if they are 180 degrees out of phase. Because no signals are being received from −(45-55) degrees, there is little or no interference with the desired signal. The element-to-element pitch 'p' with this embodiment is designed according to the following formula:

$$p = \frac{\lambda}{2 \cdot \cos(\theta_D)}$$

where lambda is the wavelength of the ultrasound within the propagation medium and theta is the desired Doppler angle.

In one embodiment, the receive circuitry shown in FIG. 11B processes the signals received by the transducer receive elements. In one embodiment, signals from the 0 and 180-degree elements are applied to a differential amplifier 650 that produces a difference between the signals or equivalently, a sum of the two signals with one channel phase-shifted 180 degrees. The output of the difference amplifier 650 is fed to a radio frequency (RF) amplifier 660 that increases the signal strength of the difference signals. The output of the RF amplifier 660 is fed to a pair of demodulators (mixers and envelope detectors) that mix the signals back to baseband using the 0 and 90-degree clock signals that are used to drive the transmit elements (FIG. 11A). The result is a pair of baseband I and Q channel signals that can processed with the components shown and described in FIG. 32 of U.S. Patent Publication No. US 2018-0353157 A1 which is incorporated by reference. Other circuits for detecting Doppler shifts from analog baseband signals could also be used.

As indicated above, one of the benefits of using a flexible phased array transducer is that it is directs and detects ultrasound signals at an angle with respect to a flat bottom surface of a patient pad. Because the bottom surface of the patient pad is generally flat and the transducer is flexible, the discomfort associated with wearing the ultrasound patch for longer periods of time is reduced. In addition, the flexibility of the transducer allows it to conform to the subject's anatomy allowing it to be used in more places than in the neck area of the subject. Finally, because of the flexibility, the transducer is also less likely to break because of accidental drops or contact etc.

As discussed above, the ultrasound patch of the disclosed technology is useful for detecting fluid flow in a vessel (e.g. artery or vein) of a subject. The readings from the sensor provide useful information to a physician, health care professional or researcher. One measurement that can be made with the disclosed transducer is an estimation of central venous pressure (CVP).

Measurement of the central venous pressure (CVP), or right atrial pressure is an important metric for venous congestion, particularly for the abdominal organs such as the kidney. As well, because the CVP is the back pressure for all venous returns, an elevated CVP raises the risk of venous congestion throughout the body. The central venous pressure waveform has been used to diagnose restrictive cardiac disease such as cardiac tamponade, constrictive pericarditis, right ventricular dysfunction, pulmonary hypertension, tricuspid regurgitation etc. Similar physiology in the hepatic veins has been used to estimate fluid responsiveness.

Figure 12:
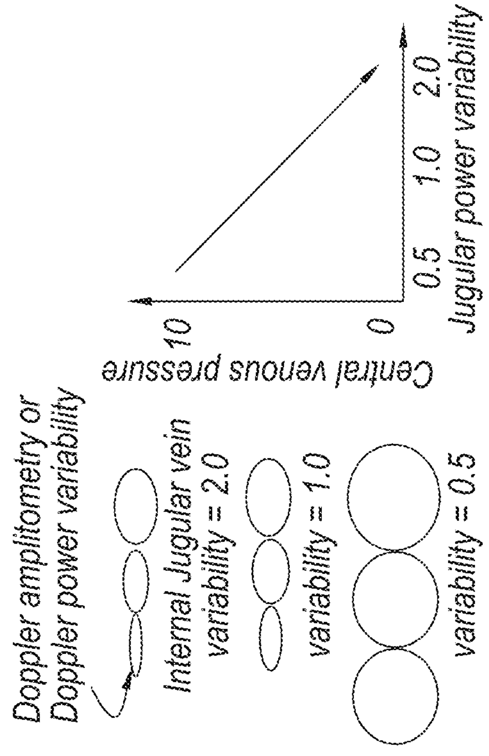
FIG. 12 is a graph of a variability in internal jugular vein diameter versus central venous pressure (CVP) during a cardiac cycle.
Figure 14:
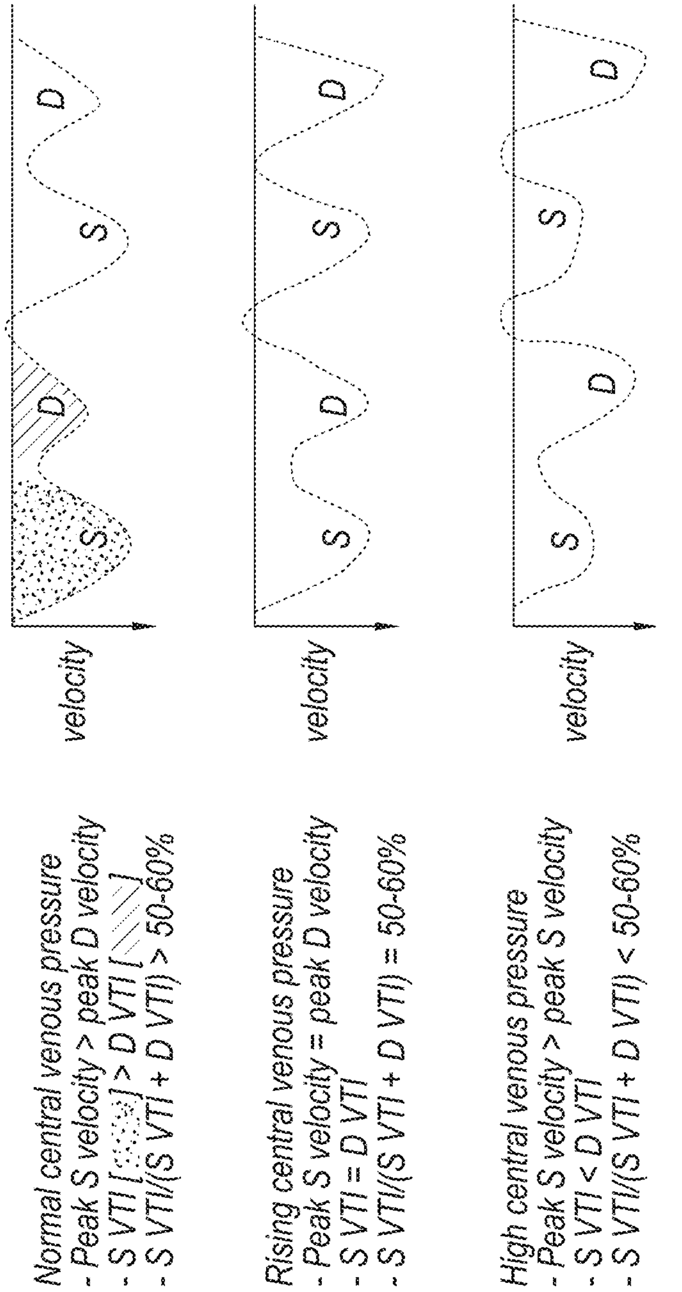
FIG. 14 are graphs of systolic and diastolic venous flow velocity time integrals (VTI) away from a transducer during cardiac cycles for normal, rising and high central venous pressures.
Figure 15:
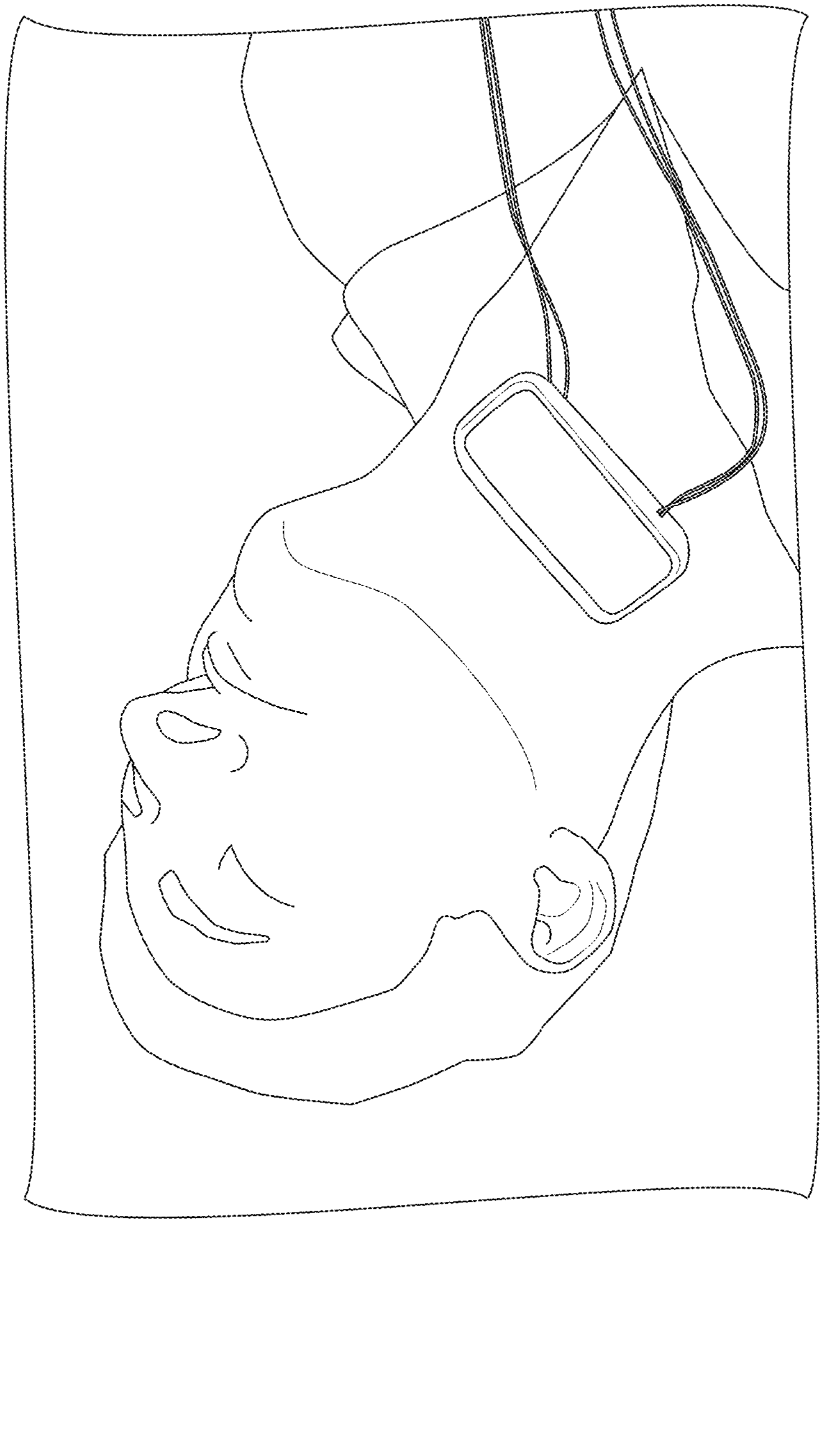
FIG. 15 illustrates a prototype ultrasound flow measuring device in position over the carotid artery of a subject.
Figure 16:
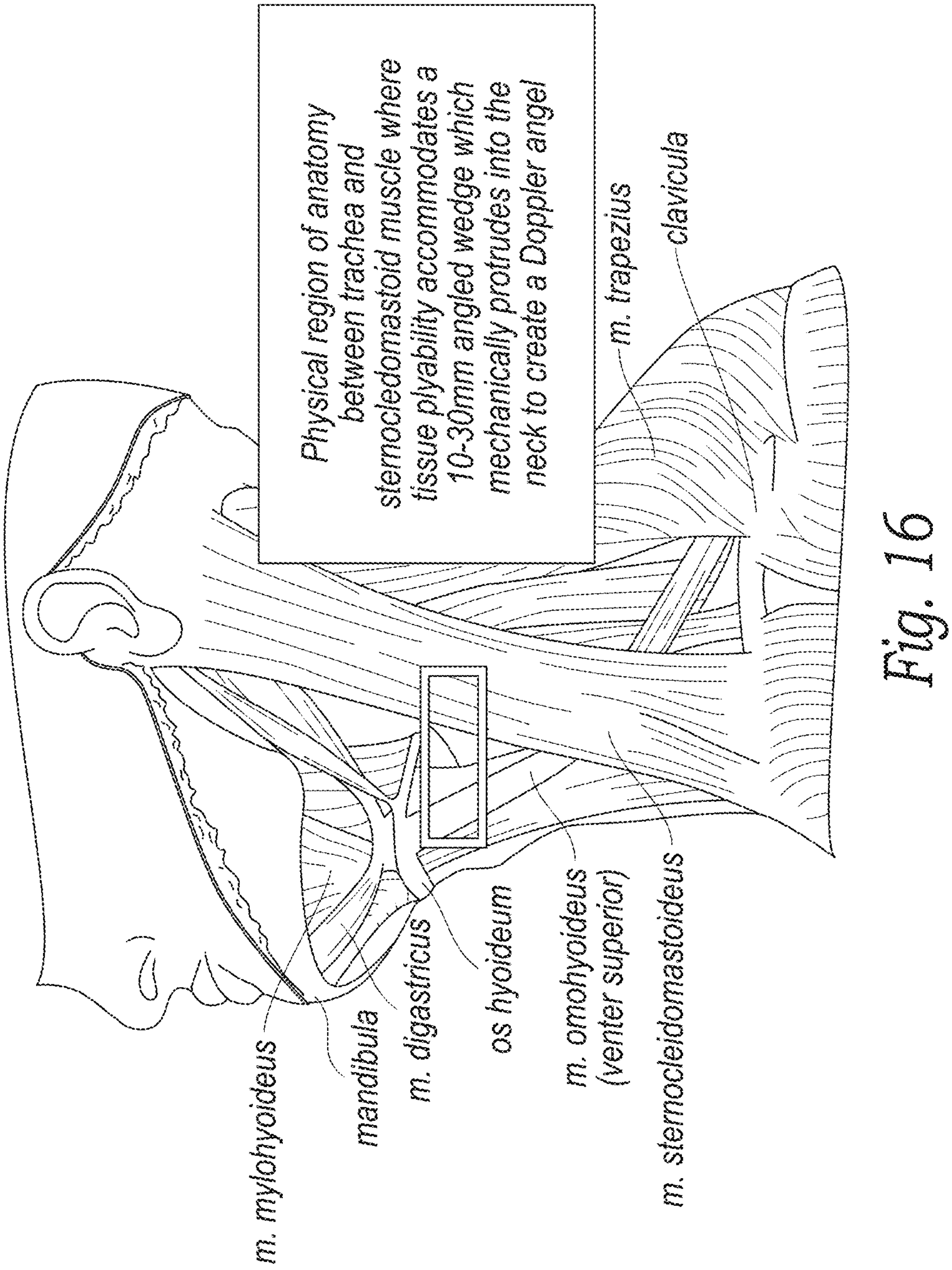
FIG. 16 is an anatomical illustration showing a physical area in which the flow measuring device in accordance with some embodiments of the disclosed technology is placed.

There are numerous means of non-invasively assessing the CVP via the jugular vein which predominantly exploit measurements of the absolute diameter of the jugular vein versus respiratory variation in the jugular vein diameter as shown in FIG. 15. The flow measuring devices of the disclosed technology measure Doppler signals that are related to vessel diameter and vessel flow. From these estimates, a correlation to central venous pressure can be made. As shown in FIG. 12, the variability of jugular vein size over the cardiac cycle has an inverse relation to central venous pressure. If the vessel changes size during the cycle by a variability of 2:1 for example, central venous pressure is low. On the other hand, if the vessel stays about the same size (variability of 0.5) then central venous pressure is higher. In another embodiment, the Doppler amplitude or Doppler power of the blood flowing though the carotid versus the jugular vein is compared and used to estimate central venous pressure as shown in FIG. 16. In this embodiment, the Doppler power of blood flow in the carotid at some point in the cardiac cycle such as peak systole, is compared with the Doppler power in the jugular at the same moment in time. If the ratio of the Doppler power in the jugular is low compared to the Doppler power in the carotid, e.g. 0.5:1, then central venous pressure is estimated to be low. On the other hand, if the ratio of the Doppler power in the jugular is high compared with the Doppler power in the carotid for example 2:1, then the central venous pressure is estimated to be high.

Figure 13:
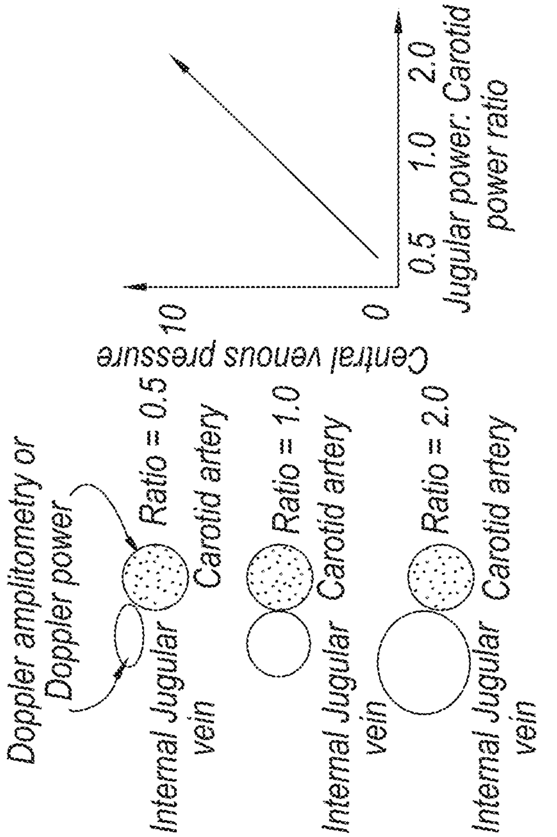
FIG. 13 is a graph of a ratio of internal jugular and carotid Doppler powers versus central venous pressure.

In the relationship shown in FIG. 13, the Doppler power or Doppler amplitude within the jugular relates to the size of the jugular vein compared to the size of the carotid at some point and has a relationship to CVP. In one embodiment, multiple Doppler amplitude or Doppler power readings for blood flowing in the jugular (reverse flow) and carotid (forward flow) are computed and stored by a processor over a cardiac cycle. Variations of more than 1.0 over a cardiac cycle may signal an increased risk for high CUP. In some embodiments, ECG signals are obtained simultaneously with the Doppler measurements to correlate the Doppler measurements with the cardiac cycle. A processor is programmed to analyze the variations in the Doppler amplitude or Doppler power over the cardiac cycle and compare against data from studies relating the Doppler amplitude and Doppler power variations to CUP. In one embodiment, the processor may store the relationship data in a memory on the ultrasound patch. In another embodiment, the processor of the ultrasound patch transmits the Doppler measurements to a remote computer over a wired or wireless link to a computer that stores the relationship data.

Jugular venous velocity profiles may be used to estimate right heart function. Jugular venous physiology has also been validated in the superior vena cava. The Doppler venous velocity profile follows the time-course of the central venous pressure waveform.

A continuous wave Doppler ultrasound patch of the types disclosed can be placed on the neck to continuously and non-invasively measure both internal jugular venous waveform velocity/morphology and Doppler power (i.e. amplitometry) in the jugular vein. This data is obtained continuously and integrated to give quantitative and qualitative assessments of the central venous pressure in a continuous and hands-free method. In one embodiment, estimates of normal, rising or high CVP are calculated by integrating the venous velocity (VTI) over the systolic (S) and diastolic (D) phases of the heart cycle. A ratio of the systolic VTI to the sum of the systolic and diastolic VTI's is used as a guide to CVP.

Figure 17:
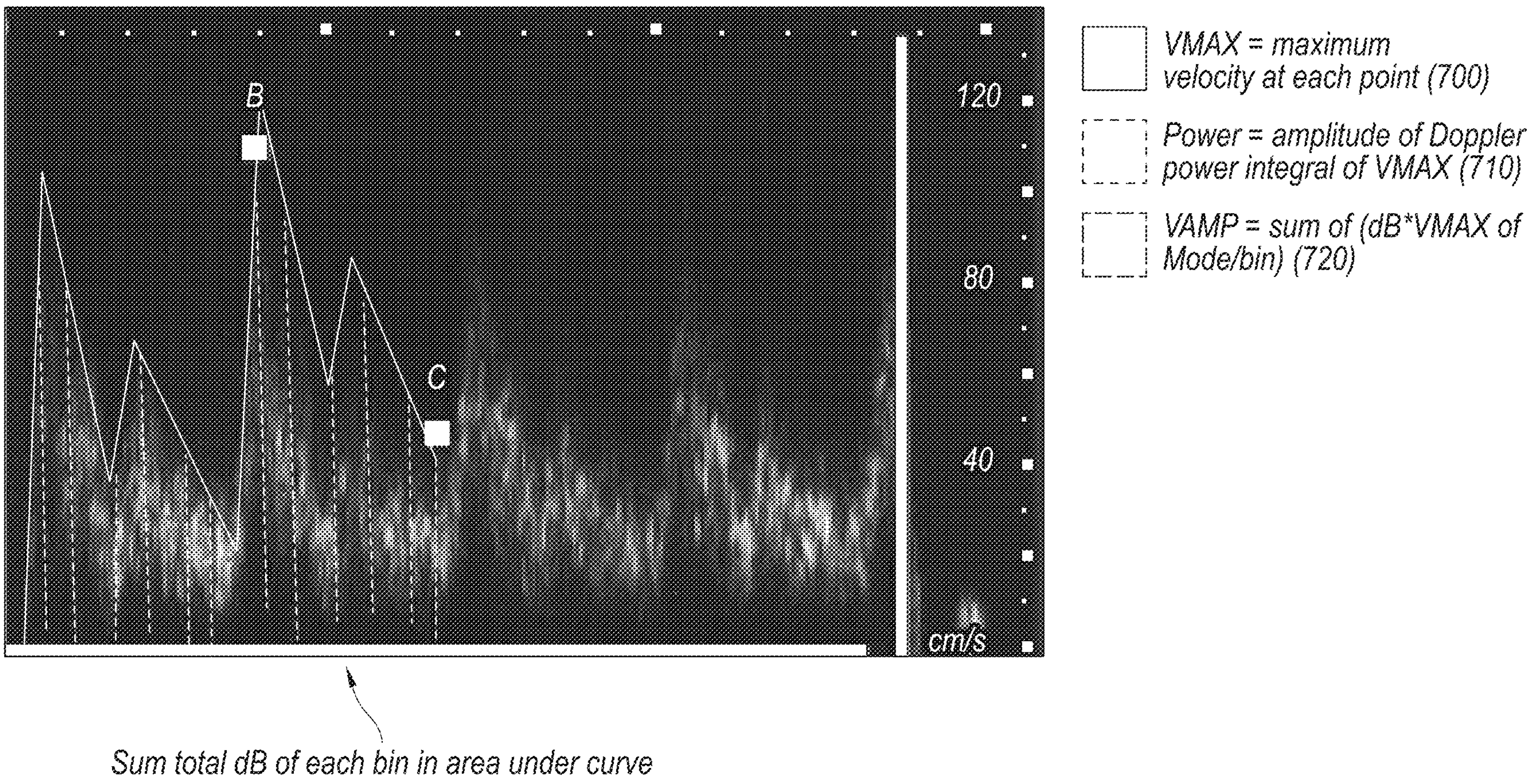
FIG. 17 shows a Doppler scan and measurements made in accordance with an embodiment of the disclosed technology.

In one embodiment, if the ratio is >60% then normal CUP is indicated. If the ratio is between 50-60%, then rising CVP is indicated and if the ratio is <50%, then high CVP is indicated as shown in FIG. 17. The particular threshold percentages may be adjusted as additional clinical data is obtained.

In one embodiment, measurements of the Doppler velocity profile of the jugular vein (or accompanying vein next to any major artery throughout the body) are continuously and non-invasively measured (over at least several cardiac cycles and preferably longer such as over several minutes or hours). The data are analyzed for systolic and diastolic peak jugular vein velocity as well as jugular vein systolic velocity time integral (VTI) relative to diastolic vein VTI as a qualitative and quantitative assessment of CVP, right ventricular function, fluid responsiveness and fluid tolerance.

In one embodiment, jugular venous Doppler power is continuously and non-invasively monitored as a surrogate for vein diameter. Continuously monitored Doppler power throughout a respiration cycle is used as a surrogate for jugular vein size, collapsibility and therefore CVP.

In one embodiment, jugular venous power is continuously and non-invasively monitored and compared to carotid artery power—also measured by the same continuous wave ultrasound patch. The comparison is used as a surrogate for relative vascular diameters and compute a ratio as a qualitative estimation of CVP.

In one embodiment, the jugular venous waveform and Doppler power are continuously and non-invasively monitored, measured and compared to carotid power and waveform to identify venous waveform abnormalities. This data is provided to an artificial intelligence engine or neural network along with clinical data to continuously refine and enhance the non-invasive measurement of the CVP and detect cardiovascular abnormalities (e.g. tricuspid regurgitation) as well as to detect both fluid responsiveness and fluid tolerance.

In one embodiment, instantaneous changes in jugular venous waveforms and jugular Doppler power in response to provocative maneuvers such as passive leg raise, fluid administration, and intravenous contrast injection (e.g. agitated saline) are measured to help assess instantaneous cardiac preload prior to interpretation of fluid responsiveness in the carotid artery and/or diagnose cardiovascular abnormalities.

An integrated approach to data capture and assessment is required in the device as each method described has varying sensitivity and specificity for estimating an elevated central venous pressure. For example, the method which has the greatest receiver operative curve statistic is an internal jugular vein area relative to carotid artery area of more than 2.0.

As disclosed in U.S. patent application Ser. No. 15/877,251 (U.S. Patent Publication No. US 2018-0353157 A1), the transducers are incorporated in a device with processing power (e.g. microprocessor or microcontroller), signal processing circuitry and memory that can record and store measurement data obtained over a period of time. The device includes circuitry to send the data to a remote computer system via a wired or wireless communication link. The data can be analyzed using artificial intelligence or other algorithms to estimate CVP. One aspect of the disclosed device is that it can record the aforementioned data for storage and analysis. The quadrature signal processing circuitry is configured to allow estimates of the fluid flow in both directions toward and away from the transducer elements corresponding to flow in the carotid and the jugular.

Because transducer pairs overlap both the carotid artery and jugular vein, measurements of flow in both vessels can be simultaneously detected and analyzed.

FIG. 15 shows a prototype flow measuring device in position on a subject's neck. With the elastomeric patient pad, the device is designed to be comfortable for extended subject flow monitoring.

FIG. 16A shows an anatomy in which the ramp on the bottom of some embodiments of the patient pad is designed to place the transducers near the carotid artery in a subject. The ramp is designed to place the transducers in the physical region between the trachea and the sternocleidomastoid muscle where tissue pliability accommodates a 10-30 mm angled wedge into the neck to create the desired Doppler angle. The ultrasound patch has transducers that are wide enough to produce a beam that intersects the carotid artery, the jugular vein or both.

FIG. 17 shows a sample Doppler signal from a subject's vessel. A line 700 on the graph shows the max flow velocity (VMAX) at each point in the cardiac cycle. A line 710 is the Doppler power of the flow at each point. In one embodiment, the power is determined by summing the power in a number of different frequency bins (e.g. 50 Hz bins) up to the maximum frequency detected at each point in time. The power at any point in time serves as surrogate for vessel diameter. A new measurement can be made by binning frequencies under the max frequency/velocity curve per unit time. In one embodiment, the measurement, VAMP 720 is made by multiplying frequency/velocity bins in a given unit of time (e.g., 10 ms) by the amplitude of the mode frequency in a bin to produce a surrogate measure of a number of red blood cells passing through the ultrasound beam and summing over all the bins present in the Doppler signal at that point in time. VAMP serves as a surrogate for flow in a vessel.

Figure 18:
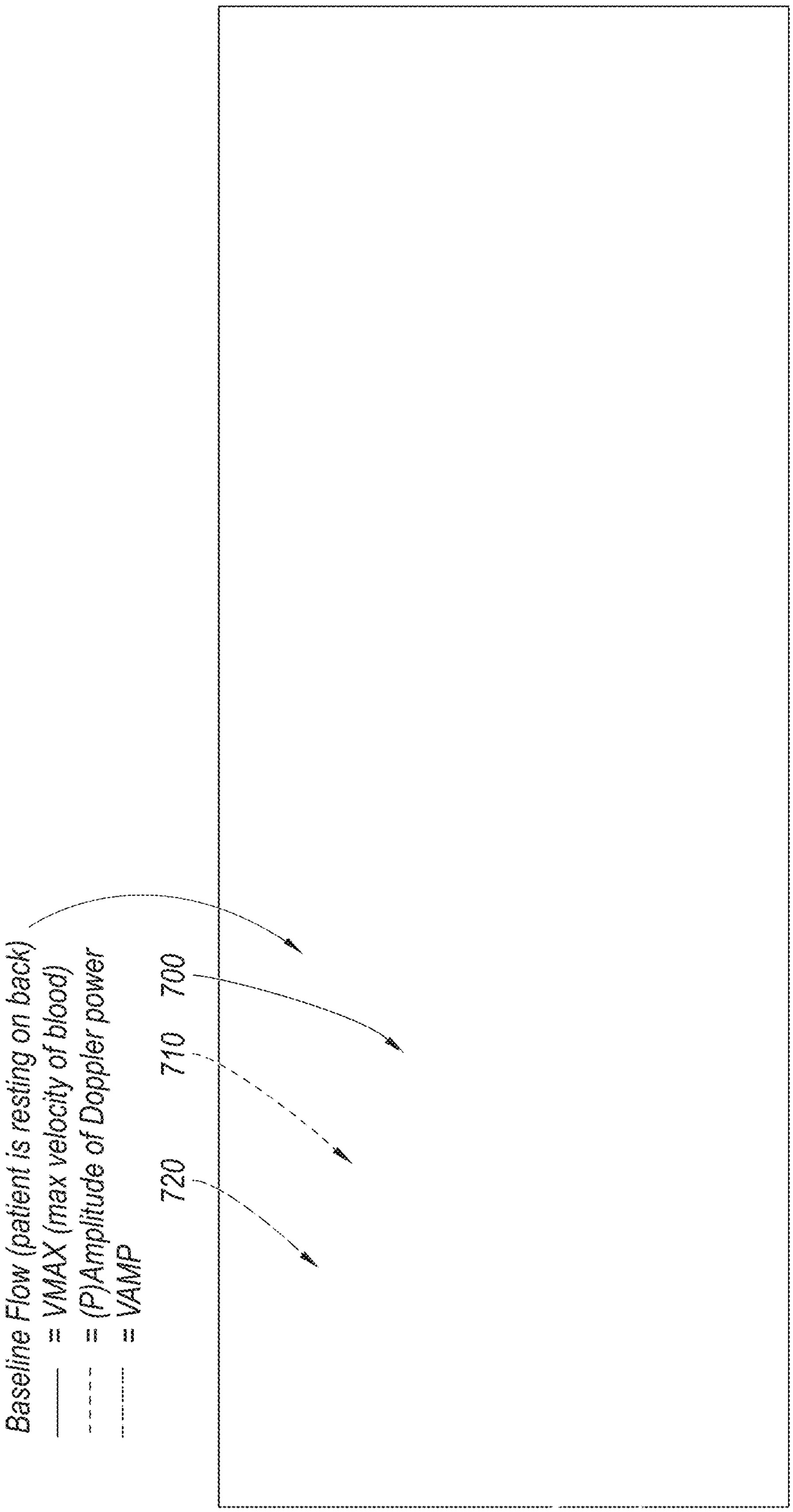
FIG. 18 shows how the measurements of Doppler power and the frequencies under a max frequency/velocity curve per unit time (VAMP) track maximum flow velocity (VMAX) in a resting state in accordance with an embodiment of the disclosed technology.
Figure 19:
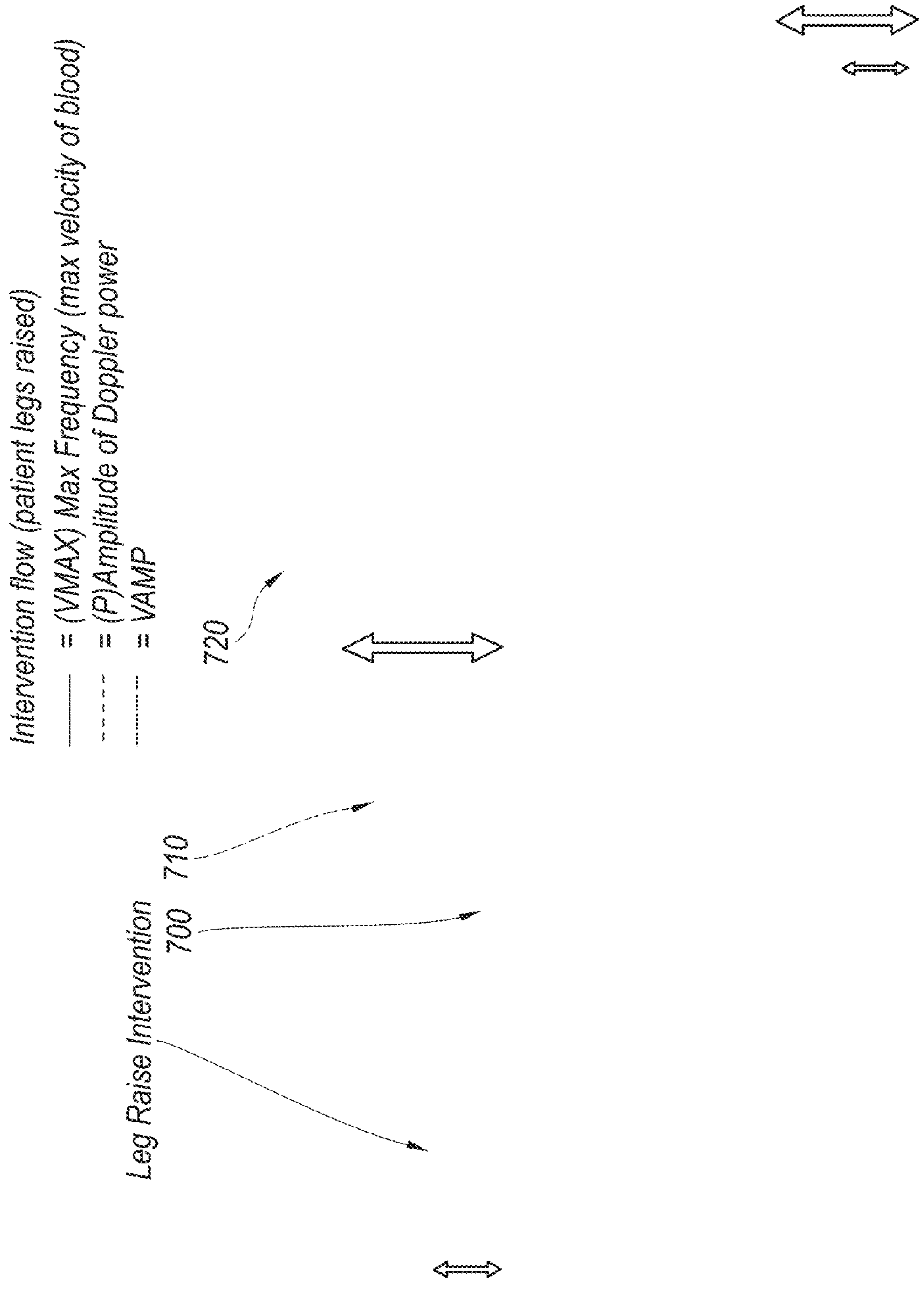
FIG. 19 shows how Doppler power and VAMP measurements vary with a fluid intervention in accordance with an embodiment of the disclosed technology.

FIG. 18 shows how VMAX, calculated power and VAMP track during a rest state. FIG. 19 shows how the calculated power 710 and VAMP 720 vary versus VMAX 700 during an interventional fluid event such as a leg raise. While the VMAX 700 stays relatively constant, the power 710 and VAMP 720 measurements increase during the event and produce useful clinical information. In one embodiment, the graphs are normalized so they can all be plotted on the same chart.

In some embodiments, the disclosed technology is useful in investigating the relationship between Doppler signals detected in the carotid or other vessels and congestive heart failure. Congestive heart failure (CHF) is the most common cause of hospitalization in adults over the age of 65 years old; the burden upon the health care system of this disease is immense. In subjects with heart failure symptoms, left ventricular systolic function is ubiquitously assessed using standard echocardiography and quantified using the ejection fraction. Importantly, an ejection fraction of less than 35-40% has major clinical implications because life-preserving pharmacological and electrophysiological therapies are indicated.

Figure 20A:
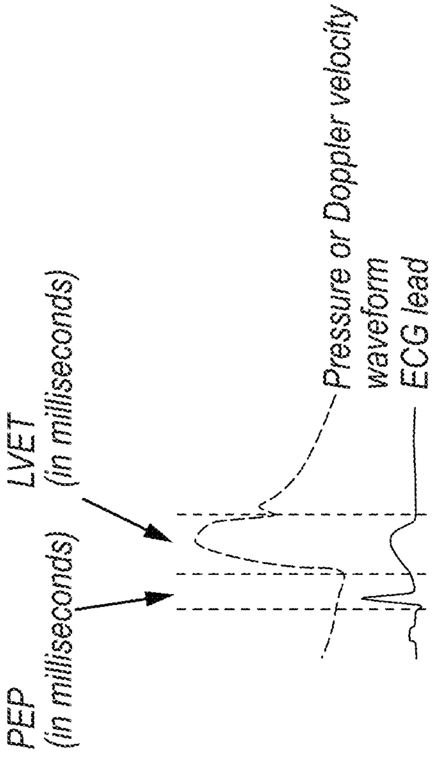
FIG. 20A shows a relationship between an electrocardiogram (ECG) signal and a Doppler velocity waveform and FIG. 20B shows an ultrasound patch with ECG electrodes to detect an ECG signal in accordance with some embodiments of the disclosed technology.

As shown in FIG. 20A, the left ventricular ejection time (LVET) is the duration (typically in milliseconds) of systole—defined on the pressure waveform from end-diastole to the dicrotic notch. In other words, the LVET is the duration that the aortic valve is open—ejecting blood into the arterial tree. Interestingly, there is a known, direct relationship between the LVET and ejection fraction; in other words, as ejection fraction falls, so too does the LVET, in milliseconds. The relationship is robust enough that authors have advocated using the LVET to monitor heart failure therapy. While the LVET has classically been measured using the pressure waveform, it has also been validated using the Doppler-derived spectrogram from both the left ventricular outflow tract and aorta and, quite notably, the common carotid artery. Accordingly, measurement of the common carotid ejection time has both diagnostic and therapeutic implications for the left ventricle.

In addition to the LVET, the aortic pre-ejection phase (PEP) has also been measured as a marker of left ventricular function. The PEP is measured as the duration—again in milliseconds—from the onset of systole on the ECG, to the upstroke in the aortic pressure waveform. As above, the PEP has also been validated using Doppler velocity in the aorta. Contrary to the LVET, the PEP has an inverse relationship with left ventricular function; that is, as the duration from the electrocardiographic impulse to the mechanical impulse rises, cardiac function is notably poorer. Given that the PEP is indirectly related to cardiac function while the LVET is directly related to cardiac function, one group created an index of PEP/LVET using aortic Doppler from a transthoracic echocardiogram and found an excellent association with left ventricular ejection fraction; further, some therapies may be specifically-monitored using the PEP/LVET ratio.

Figure 20B:
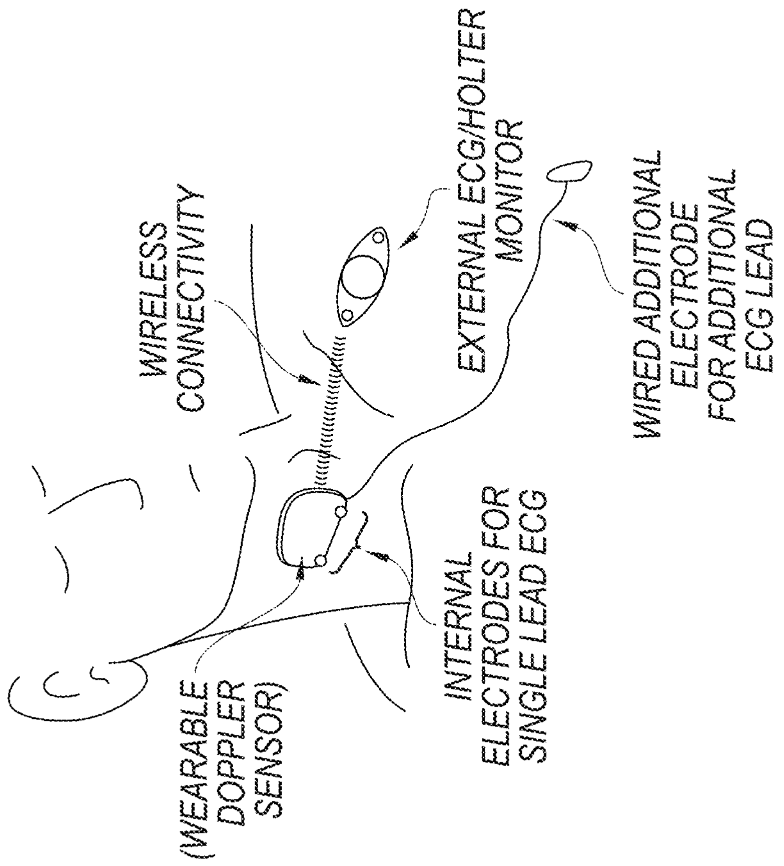

As shown in FIG. 20B, in some embodiments, the disclosed ultrasound patch includes one or more integrated or connected ECG electrodes to detect a subject's ECG signals. Circuitry within the patch conditions the ECG signals for wired or wireless communication to a remote device such as an ECG detector along with ultrasound signals detected from a subject's vessel. A processor within the patch can also be programmed to analyze the detected ECG signals to measure the PEP, systolic ejection time, PEP/LVET ratio as well as other combinations of electrophysiological and Doppler indices as markers of left ventricular function.

While the above-mentioned indices have been found helpful in diagnosis of depressed left ventricular function, their diagnostic abilities are not perfect and could be refined. Additionally, other aspects of the carotid waveform may help predict cardiac ejection fraction. Artificial intelligence and machine learning could greatly improve the above-mentioned predictive metrics pulled from a wearable ultrasound patch with integrated ECG functionality. Additional, cryptic indices could be assessed and analyzed with respect to cardiac function, given that the morphology of the Doppler waveform is also determined by downstream vascular impedance. Artificial intelligence may serve to pull out the effects of both cardiac function and vascular impedance on the pulse of a major artery like the carotid.

In some embodiments, the ultrasound patch described above is continuous wave, rather than pulsed wave, such that the velocity profiles of the entire carotid lumen may be obtained. With this enriched data, additional parameters such as spectral broadening and maximum-to-mean velocity profiles may be captured and scrutinized in the healthy and CHF populations. For example, in healthy adults the maximum-to-mean velocity in the carotid during early systole/ejection is known to be nearly 1:1, i.e. adopt a 'plug like' profile. This is likely not the same with impaired cardiac contractility. Additionally, power or amplitude profiles of the blood may change with diuretic-induced hemoconcentration or other pharmacological interventions—all such metrics may be teased apart with advanced machine learning.

Figure 21:
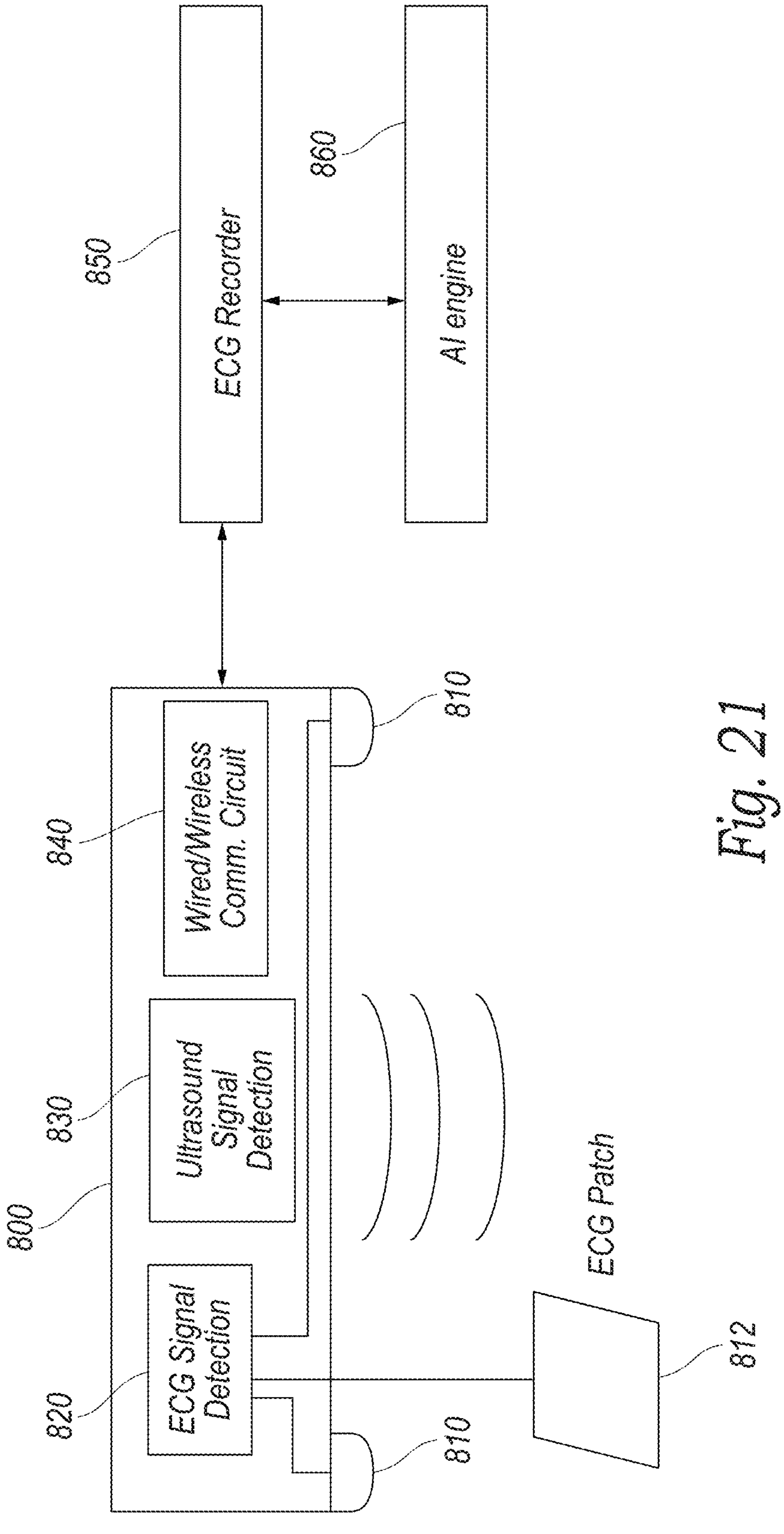
FIG. 21 is a block diagram of a system including an ultrasound patch with one or more ECG electrodes that provide an ECG signal to an ECG recorder to correlate detected Doppler signals with ejection fraction or other cardiac output measures in accordance with some embodiments of the disclosed technology.

To investigate these relationships, some embodiments of the ultrasound patch include integrated or connected ECG electrodes to measure a subject's electrocardiogram. As shown in FIG. 21, the ultrasound patch 800 includes one or more integrated ECG electrodes 810 and may be connected to one or more remote ECG electrodes 812. ECG signal detection circuitry 820 within the ultrasound patch receives and conditions ECG signals captured by the electrodes. In some embodiments, a processor (not shown) analyzes the signals to measure portions of the signals such as PEP, systolic ejection time etc. Ultrasound detection circuitry 830 captures Doppler signals from a vessel of interest. The Doppler and ECG signals are transmitted via a wired or wireless communication circuit 840 to a remote device such as an ECG recorder 850. In some embodiments, the Doppler and ECG data are analyzed by an artificial intelligence engine 860 that is programmed to correlate Doppler and EGC signals with CHF or other medical conditions.

Data acquired from a wearable, continuous wave ultrasound patch over the common carotid artery may be analyzed and integrated to greatly improve both diagnostic and therapeutic facets of congestive heart failure—especially if integrated with an imbedded electrocardiogram. A convenient-to-apply ultrasound patch can improve access to care in underserved communities where cardiologists and echocardiographers are unavailable. By similar reasoning, remote monitoring of CHF therapy will be enhanced.

Figure 22:
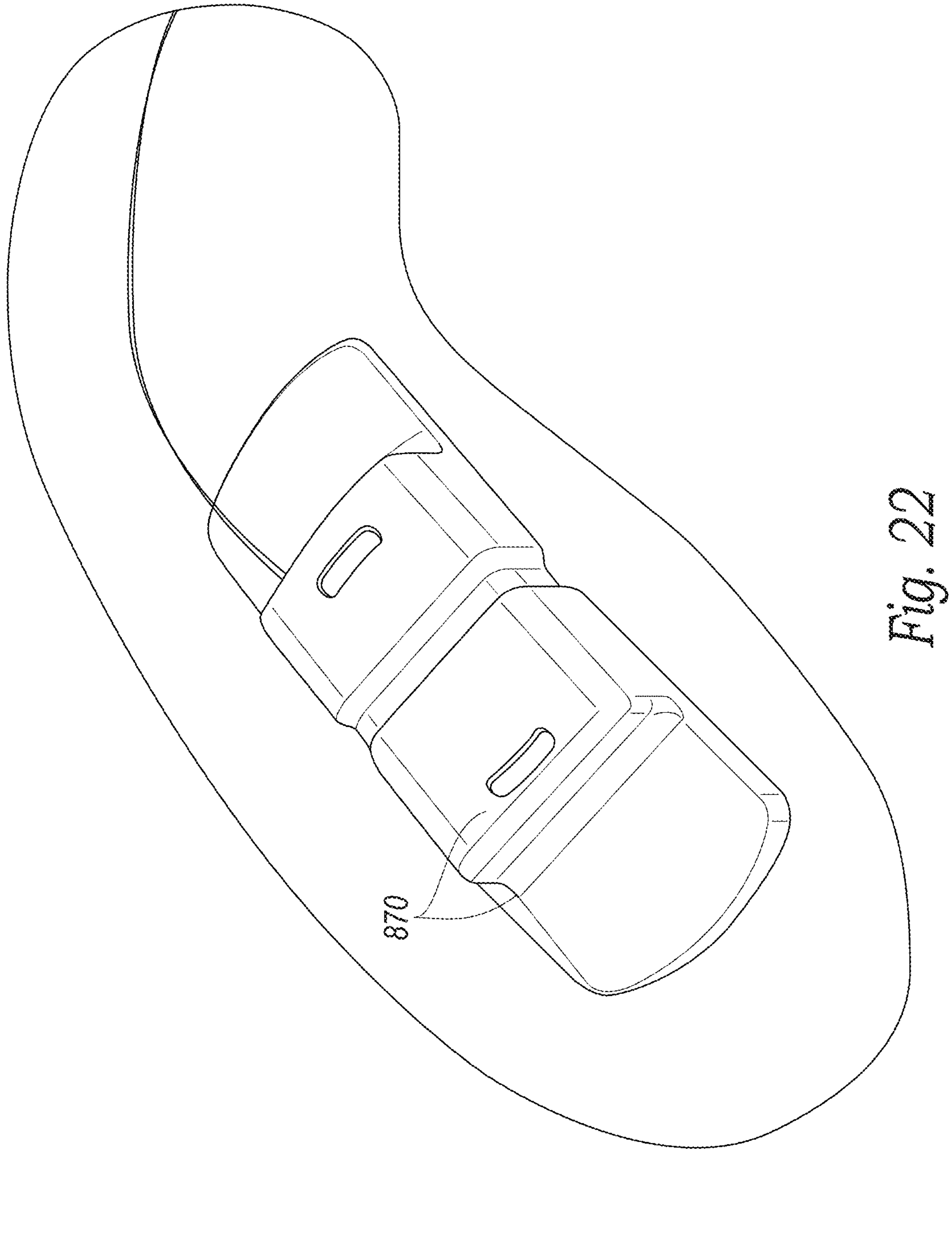
FIG. 22 shows an embodiment of an ultrasound patch with slots in a housing to receive a strap that secures the patch to a subject in accordance with some embodiments of the disclosed technology.

In some embodiments, the ultrasound patch is to remain on a subject for a period of time and can be prone to coming out of contact with the subject's skin. In one embodiment shown in FIG. 22, each end of the housing for the ultrasound patch includes two openings or slots 870 on a top and side surface thereof through which a tracheostomy strap (not shown) can be passed in order to secure the patch to the subject. Tracheostomy straps generally include a pad that fits behind the neck and two self-adhering straps (such as hook and loop straps e.g. Velcro®). The slots 870 on the ends of the housing allow the straps to be passed through a corner of the housing and folded and secured back on themselves to secure the patch against a subject's neck (or other anatomy such as the wrist, thigh, knee, ankle etc.) Other configurations to secure the strap besides an opening could be used such as a bar extending outwardly from the housing that the strap can fit underneath if it is desirable to maintain a water-resistant housing.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. An ultrasound patch configured for use on the skin of a patient to detect fluid flow in a vessel in the patient, comprising:

one or more piezoelectric transmit elements;

one or more piezoelectric receive elements adjacent the one or more piezoelectric transmit elements;

a housing that encloses electronics, the electronics in communication with the one or more piezoelectric transmit and receive elements, the housing including a top surface and bottom surface opposite the top surface, the top surface configured to face away from the skin of the patient and the bottom surface configured to face toward the skin of the patient during use with the patient;

a flexible engagement layer having a first side opposite a second side, the first side of the flexible engagement layer coupled to the housing and positioned to hold the bottom surface of the housing facing toward the skin of the patient, and the second side configured to engage the skin of the patient; and a ramp coupled to the flexible engagement layer on the second side, wherein the ramp extends away from the top surface, the bottom surface and the flexible engagement layer toward the patient, the ramp having at least one wall sloped at an angle relative to the bottom surface, the ramp supporting the one or more piezoelectric transmit and receive elements adjacent to the at least one wall, and the one or more piezoelectric transmit elements positioned to transmit in a direction away from the top surface and the bottom surface and toward the vessel in the patient.

2. The ultrasound patch of claim 1, wherein the angle is about 30 degrees.

3. The ultrasound patch of claim 1, wherein the at least one wall comprises a first wall and a second wall, and wherein the angle is a first angle, and the first wall is sloped at the first angle, and the second wall is sloped at a second angle relative to the bottom surface.

4. The ultrasound patch of claim 1, wherein the one or more piezoelectric transmit elements are supported at a first angular orientation relative to a plane of the bottom surface of the housing, and the one or more receive elements are held at a second angular orientation relative to the plane of the bottom surface of the housing, wherein the first and the second angular orientations are different.

5. The ultrasound patch of claim 1, wherein the one or more piezoelectric transmit and receive elements are mounted to a circuit board having a slot behind the one or more piezoelectric transmit and receive elements to provide an air gap behind the one or more piezoelectric transmit and receive elements and wherein the ramp includes a recess into which the circuit board is fitted.

6. The ultrasound patch of claim 1, wherein the ramp is sized to fit within a space between a sternocleidomastoid muscle and a trachea of the patient and is symmetrically placed between ends of the housing along a long dimension of the housing enabling placement on either side of the patient's neck.

7. The ultrasound patch of claim 1, further comprising one or more electrocardiogram (ECG) electrodes that are configured to detect an ECG signal from the patient.

8. The ultrasound patch of claim 1, further comprising ECG signal detection circuitry configured to detect an ECG signal from a remote ECG electrode on the patient.

9. The ultrasound patch of claim 8, further comprising:

ultrasound detection circuitry configured to capture Doppler signals from the vessel; and a communication circuit configured to transmit the ECG signal and the Doppler signals to a remote device.

10. The ultrasound patch of claim 1, further comprising a processor that is configured to detect a power of Doppler flow in an artery and a power of Doppler flow in a vein and to compare the powers as an estimate of central venous pressure.

11. An ultrasound patch configured to detect fluid flow in a vessel, comprising:

a flexible phased array transducer including a number of transmit elements and a number of receive elements, wherein the transmit elements and the receive elements comprise a number of piezoelectric pillars that are joined with a flexible adhesive, wherein the transmit elements are connected to a first common electrode and the receive elements are connected to a second common electrode different than the first common electrode, and the first and second common electrodes are deposited on one side of the piezoelectric pillars, and wherein the first and second common electrodes include connectors located at either end of the flexible phased array transducer and are configured to supply signals to the transmit elements or receive signals from the receive elements;

a flexible circuit board including electrical connections on a first side of the flexible circuit board, the electrical connections interconnecting with the connectors of the flexible phased array transducer, wherein the flexible circuit board includes an opening through which ultrasound signals generated by the transmit elements can pass through from the first side of the flexible circuit board toward a second side of the flexible circuit board;

a patient pad including a patient contacting surface interconnected with the first side of the flexible circuit board, wherein the flexible phased array transducer and the flexible circuit board are configured to align in a direction generally parallel with a plane of the patient contacting surface; and transmit electronics configured to produce differently phased driving signals to the transmit elements such that an ultrasound beam is transmitted at an angle with respect to the plane of the patient contacting surface of the patient pad.

12. The ultrasound patch of claim 11, wherein the flexible phased array transducer is encapsulated in the patient pad with an air gap behind the transmit elements and the receive elements.

13. The ultrasound patch of claim 11, wherein the transmit electronics are configured to drive adjacent ones of the transmit elements with signals at 0, 270, 90 and 180 degrees out of phase with respect to a reference signal such that the ultrasound beam is transmitted at the angle with respect to the plane of the patient contacting surface of the patient pad.

14. The ultrasound patch of claim 11, wherein the receive elements comprise a greater number of the piezoelectric pillars in a width dimension than the transmit elements.

15. The ultrasound patch of claim 14, wherein a width of the receive elements is twice a width of the transmit elements.

16. The ultrasound patch of claim 11, wherein the transmit electronics are in a housing and the housing includes openings through the housing that are configured to receive a strap to secure the housing and the patient pad to a subject.

17. The ultrasound patch of claim 11, wherein the patient pad includes one or more ECG electrodes that are configured to detect an ECG signal from a subject.

18. The ultrasound patch of claim 17, further comprising ECG signal detection circuitry that is configured to detect an ECG signal from a remote ECG electrode on the subject.

19. The ultrasound patch of claim 11, further comprising a processor that is configured to detect a power of Doppler flow in an artery and a power of Doppler flow in a vein and to compare the powers as an estimate of central venous pressure.

20. The ultrasound patch of claim 11, wherein the flexible phased array transducer is symmetrically positioned between ends of the patient pad along a long dimension of the patient pad.

* * * * *